United States Patent
Saiki

(10) Patent No.: US 7,897,398 B2
(45) Date of Patent: Mar. 1, 2011

(54) CENTRIFUGAL ANALYSIS DEVICE WITH IMPROVED MIXING AND METHOD USING THE DEVICE

(75) Inventor: Hiroshi Saiki, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/664,758

(22) PCT Filed: Jul. 25, 2008

(86) PCT No.: PCT/JP2008/001985
§ 371 (c)(1),
(2), (4) Date: Dec. 15, 2009

(87) PCT Pub. No.: WO2009/016811
PCT Pub. Date: Feb. 5, 2009

(65) Prior Publication Data
US 2010/0184228 A1    Jul. 22, 2010

(30) Foreign Application Priority Data
Jul. 27, 2007    (JP) .................................. 2007-195283

(51) Int. Cl.
G01N 35/00    (2006.01)
G01N 21/07    (2006.01)
B04B 5/02    (2006.01)

(52) U.S. Cl. ............. 436/45; 422/72; 422/100; 436/165; 436/172; 436/179; 436/180; 494/10; 494/16; 494/43

(58) Field of Classification Search .................... 422/72, 422/100; 436/43, 45, 164–165, 172, 179–180; 494/10, 16, 43
See application file for complete search history.

(56) References Cited

U.S. PATENT DOCUMENTS

| | | | | | |
|---|---|---|---|---|---|
| 3,899,296 | A | * | 8/1975 | Mailen et al. | 422/50 |
| 4,284,602 | A | * | 8/1981 | Kelton et al. | 422/72 |
| 4,632,908 | A | * | 12/1986 | Schultz | 436/157 |
| 4,743,558 | A | * | 5/1988 | Guigan | 436/45 |
| 4,814,282 | A | * | 3/1989 | Holen et al. | 436/165 |
| 4,857,274 | A | * | 8/1989 | Simon | 422/72 |
| 4,894,204 | A | * | 1/1990 | Cornut | 422/72 |
| 5,061,381 | A | * | 10/1991 | Burd | 210/789 |
| 5,061,446 | A | * | 10/1991 | Guigan | 422/64 |
| 5,089,417 | A | * | 2/1992 | Wogoman | 436/45 |
| 5,122,284 | A | * | 6/1992 | Braynin et al. | 210/782 |
| 5,147,607 | A | * | 9/1992 | Mochida | 422/57 |
| 5,160,702 | A | * | 11/1992 | Kopf-Sill et al. | 422/72 |
| 5,173,262 | A | * | 12/1992 | Burtis et al. | 422/72 |

(Continued)

FOREIGN PATENT DOCUMENTS

JP    3-223674    10/1991

(Continued)

*Primary Examiner* — Arlen Soderquist
(74) *Attorney, Agent, or Firm* — Hamre, Schumann, Mueller & Larson, P.C.

(57) ABSTRACT

A device for analysis used for transferring a solution to a measurement spot 38 by a centrifugal force and reading in which a reaction liquid located at the measurement spot 38 is optically accessed. An operation cavity 30 and a receiving cavity 32 are arranged from the upstream side to the downstream side of the transfer. The operation cavity 30 and the receiving cavity 32 communicate with each other via a connection section 59 to transfer the solution of the operation cavity 30 to the receiving cavity 32. The connection section 59 is located inside the liquid level of a diluted solution retained in the operation cavity 30, relative to a rotation axis 102.

18 Claims, 23 Drawing Sheets

U.S. PATENT DOCUMENTS

| | | | |
|---|---|---|---|
| 5,186,844 A * | 2/1993 | Burd et al. | 210/782 |
| 5,320,808 A * | 6/1994 | Holen et al. | 422/64 |
| 5,472,603 A * | 12/1995 | Schembri | 210/380.1 |
| 5,591,643 A * | 1/1997 | Schembri | 436/45 |
| 5,627,041 A | 5/1997 | Shartle | 435/7.24 |
| 5,919,711 A * | 7/1999 | Boyd et al. | 436/178 |
| 6,002,475 A * | 12/1999 | Boyd et al. | 356/246 |
| 6,013,513 A * | 1/2000 | Reber et al. | 435/288.5 |
| 6,143,247 A * | 11/2000 | Sheppard et al. | 422/63 |
| 6,143,248 A * | 11/2000 | Kellogg et al. | 422/72 |
| 6,153,148 A * | 11/2000 | Thomas | 422/72 |
| 6,299,839 B1 * | 10/2001 | Karunaratne et al. | 422/63 |
| 6,319,469 B1 * | 11/2001 | Mian et al. | 422/64 |
| 6,348,176 B1 * | 2/2002 | Hammer et al. | 422/64 |
| 6,632,399 B1 * | 10/2003 | Kellogg et al. | 422/72 |
| 6,720,187 B2 * | 4/2004 | Bedingham et al. | 436/45 |
| 6,806,088 B2 * | 10/2004 | Howard | 436/45 |
| 7,384,602 B2 * | 6/2008 | Nagaoka et al. | 422/68.1 |
| 7,390,464 B2 * | 6/2008 | Kido et al. | 422/102 |
| 7,582,259 B2 * | 9/2009 | Ogawa et al. | 422/72 |
| 7,662,340 B2 * | 2/2010 | Nagaoka et al. | 422/72 |
| 7,678,576 B2 * | 3/2010 | Sasaki et al. | 436/45 |
| 7,727,472 B2 * | 6/2010 | Nagaoka et al. | 422/68.1 |
| 7,790,110 B2 * | 9/2010 | Cho et al. | 422/72 |
| 7,811,519 B2 * | 10/2010 | Shiga | 422/72 |

FOREIGN PATENT DOCUMENTS

| | | |
|---|---|---|
| JP | 5-508709 | 12/1993 |
| JP | 3061414 | 4/2000 |
| JP | 2007-10435 | 1/2007 |
| JP | 2007-24851 | 2/2007 |
| JP | 2007-78676 | 3/2007 |
| WO | 91/18656 | 12/1991 |

* cited by examiner

AA-AA

B-B

C-C

D-D

E-E

CENTRIFUGAL ANALYSIS DEVICE WITH IMPROVED MIXING AND METHOD USING THE DEVICE

TECHNICAL FIELD

The present invention relates to a device for analysis which is used for analyzing a liquid collected from an organism and the like and an analyzing apparatus and method using the device, and specifically relates to a technique for transferring a solution mixed in the device for analysis to the subsequent step.

BACKGROUND ART

In the prior art, a liquid collected from an organism and the like is analyzed by a known method using a device for analysis in which a liquid path is formed. The device for analysis can control a fluid by using a rotating device. The device for analysis can measure a solution, separate solid constituents, transfer and distribute a separated fluid, and mix a solution and a reagent by using a centrifugal force, thereby conducting a variety of biochemical analyses.

As shown in FIG. 23, a device for analysis 246 for transferring a solution by using a centrifugal force according to the prior art includes a sample chamber 248 having an inlet port 250, a diluent chamber 252 formed next to the sample chamber 248, a mixing chamber 254 disposed outside the sample chamber 248 and the diluent chamber 252 relative to the radial direction, and a separation chamber 260 which receives a solution mixed in the mixing chamber 254, through a flow limiting path 262 connected to a position in contact with the solution of the mixing chamber 254. Analysis chambers 268 are connected to a flow path 266 connected to the separation chamber 260.

During transfer, a sample to be tested is introduced into the sample chamber 248 through the inlet port 250, a diluent for diluting the sample is introduced into the dilution chamber 252, and then the sample and the diluent are both transferred into the mixing chamber 254 by a rotation of the device for analysis 246. In this configuration, the sample and diluent transferred into the mixing chamber 254 are prevented from being immediately transferred to the separation chamber 260 through the flow limiting path 262 serving as a capillary path. While the sample and the diluent are contained in the mixing chamber 254, the device for analysis 246 is reversely rotated or the rotation speed of the device for analysis 246 is increased or reduced in the same direction, so that the sample and the diluent are mixed. Patent Document 1: Japanese Patent No. 3061414

DISCLOSURE OF THE INVENTION

Problems to be Solved by the Invention

However, when the sample and the diluent are stirred in the mixing chamber 254 by reversing the rotation or increasing or reducing the rotation speed, the solution may not be sufficiently stirred and flow into the separation chamber 260 through the flow limiting path 262, so that analyses may be conducted after insufficient stirring and result in varying analysis results.

The present invention has been devised to solve the problem of the prior art. An object of the present invention is to provide a device for analysis by which a sample, a diluent, and a reagent can be fully stirred in a mixing chamber even when transferred at different times, and a mixed solution can be transferred to the subsequent step at a necessary time, and an analyzing apparatus and method using the device.

Means for Solving the Problems

A device for analysis according to a first aspect of the present invention has a micro channel structure for transferring a solution to a measurement spot by a centrifugal force and is used for reading in which a reaction liquid at the measurement spot is optically accessed, the device including: an operation cavity and a receiving cavity which are arranged from the upstream side to the downstream side of the transfer; and a connection section for communicating the operation cavity and the receiving cavity to transfer a solution in the operation cavity to the receiving cavity, the connection section being located inside the liquid level of the solution retained in the operation cavity, relative to a rotation axis for generating the centrifugal force.

A device for analysis according to a second aspect of the present invention has a micro channel structure for transferring a solution by a centrifugal force, the device including: a first retaining section for retaining a sample solution; a second retaining section for retaining a diluent; a third retaining section for receiving the sample solution and the diluent from the first and second retaining sections; a fourth retaining section which communicates with the third retaining section through a connection section and receives a diluted solution from the third retaining section; and a measurement spot which is formed on the downstream side of the transfer from the fourth retaining section, retains a reagent, and retains a reaction liquid obtained by a reaction after the reagent is dissolved by the diluted solution received from the fourth retaining section, wherein the reaction liquid at the measurement spot is optically accessed for reading and the connection section for communicating the third retaining section and the fourth retaining section is located inside the liquid level of the diluted solution retained in the third retaining section, relative to a rotation axis for generating the centrifugal force.

A device for analysis according to a third aspect of the present invention, in the second aspect, includes: between the fourth retaining section and the measurement spot, a retaining cavity which receives the diluted solution from the fourth retaining section through a connection flow path and retains a specified amount of the diluted solution; a connection flow path for communicating the retaining cavity and the measurement spot; and a second measurement spot which is formed on the downstream side of the transfer from the measurement spot, retains the reagent, and retains the reaction liquid obtained by the reaction after the reagent is dissolved by the solution received from the measurement spot, wherein a second connection section for communicating the measurement spot and the downstream side of the transfer is located inside the liquid level of the solution retained at the measurement spot, relative to the rotation axis for generating the centrifugal force.

A device for analysis according to a fourth aspect of the present invention, in the third aspect, including a third measurement spot which is formed on the downstream side of the transfer from the second measurement spot, retains the reagent, and retains the reaction liquid obtained by the reaction after the reagent is dissolved by the solution received from the second measurement spot, wherein a third connection section for communicating the second measurement spot and the downstream side of the transfer is located inside the liquid level of the solution retained at the second measurement spot, relative to the rotation axis for generating the centrifugal force.

A device for analysis according to a fifth aspect of the present invention, in the first aspect, wherein the fourth retaining section, the retaining cavity, and the second connection section are formed with cross-sectional dimensions in a thickness direction for generating a capillary force and a specified amount of the solution is collected by the capillary force.

A device for analysis according to a sixth aspect of the present invention, in the first aspect, wherein the receiving cavity collects a predetermined amount of the solution by a force of gravity generated by inclination.

A device for analysis according to a seventh aspect of the present invention, in the first aspect, wherein the receiving cavity collects a predetermined amount of the solution by an inertial force generated by swinging and a force of gravity generated by inclination.

An analyzing apparatus according to an eighth aspect of the present invention, in which the device for analysis having collected a sample solution according to the first aspect is set, including: a rotation driving device for rotating the device for analysis about the axis; and an analyzing device for conducting an analysis by optically accessing the solution in the device for analysis which has been transferred by the rotation driving device, wherein the axis is inclined and the solution retained in the operation cavity is transferred to the receiving cavity by an inertial force and a force of gravity.

An analyzing apparatus according to a ninth aspect of the present invention, in which the device for analysis having collected a sample solution according to the first aspect is set, including: a rotation driving device for rotating the device for analysis about the axis; and an analyzing device for conducting an analysis by optically accessing the solution in the device for analysis which has been transferred by the rotation driving device, wherein the axis is inclined and the solution retained in the operation cavity is transferred to the connection section of the operation cavity and the receiving cavity by a force of gravity.

An analyzing apparatus according to a tenth aspect of the present invention, in which the device for analysis having collected a sample solution according to the first aspect is set, including: a rotation driving device for rotating the device for analysis about the axis; and an analyzing device for conducting an analysis by optically accessing the solution in the device for analysis which has been transferred by the rotation driving device, wherein the axis is inclined and the solution retained in the operation cavity is transferred to the receiving cavity by a force of gravity.

An analyzing apparatus according to an eleventh aspect of the present invention, in which the device for analysis having collected a sample solution according to the first aspect is set, including: a rotation driving device for rotating the device for analysis about the axis; and an analyzing device for conducting an analysis by optically accessing the solution in the device for analysis which has been transferred by the rotation driving device, wherein the axis is inclined and the solution retained in the operation cavity is transferred to the connection section of the receiving cavity by an inertial force and a force of gravity.

An analyzing apparatus according to a twelfth aspect of the present invention, in any one of the eighth to eleventh aspects, wherein the device for analysis is movable to a position where the connection section of the receiving cavity and the operation cavity is located under the operation cavity when viewed from the front of the device for analysis.

An analyzing apparatus according to a thirteenth aspect of the present invention, in any one of the eighth to eleventh aspects, wherein the axis is inclined and the device for analysis is swung about the axis at a position where the connection section is located under the operation cavity when viewed from the front of the device for analysis.

An analyzing apparatus according to a fourteenth aspect of the present invention, in any one of the eighth to eleventh aspects, wherein the device for analysis is swung about the axis at any rotational position.

An analyzing apparatus according to a fifteenth aspect of the present invention, in any one of the eighth to eleventh aspects, wherein the axis has an angle of inclination that is optionally settable.

An analyzing apparatus according to a sixteenth aspect of the present invention, in any one of the eighth to eleventh aspects, wherein the axis has an angle of inclination of 0° to 45°.

An analyzing method according to a seventeenth aspect of the present invention is an analyzing method using the device for analysis according to the first aspect, the method including: setting the device for analysis on a rotor having an axis inclined by a predetermined angle, rotating the rotor to transfer, to the operation cavity, a diluent and a sample solution applied to the device for analysis and mix the diluent and the sample solution; moving the rotor such that the connection section of the receiving cavity and the operation cavity of the device for analysis is located under the operation cavity when viewed from the front of the device for analysis, and vibrating the device for analysis at a stop position to swingingly transfer a diluted solution having been diluted by the mixing to the downstream side of a transfer path; rotating the rotor to collect a fixed amount of the diluted solution, dissolving the sample solution stored at the measurement spot with the solution received at the measurement spot after the swinging transfer performed by rotating the rotor or vibrating the device for analysis, and stirring the sample solution; and rotating the rotor to optically access the reaction liquid at the measurement spot when the measurement spot is located at a reading position.

An analyzing method according to an eighteenth aspect of the present invention, in the seventeenth aspect, further including: rotating the rotor to collect the fixed amount of the diluted solution, repeating the swinging transfer, in which the rotor is rotated or the device for analysis is vibrated, to sequentially transfer the reaction liquid to the measurement spots on the downstream side out of the plurality of measurement spots connected in series along the transfer path; and conducting a measurement by optically accessing the measurement spot every time the reaction liquid reaches the measurement spot.

ADVANTAGE OF THE INVENTION

According to a device for analysis and an analyzing apparatus and method using the device of the present invention, solutions transferred at different times can be transferred to the subsequent process at a necessary time, so that the solutions can be transferred to the subsequent process after completely mixed and the accuracy of analysis can be improved. Further, since the solutions can be transferred to the subsequent process at a necessary time, the present invention can be also used as a device which controls transfer other than mixing and can simplify a transfer sequence and a flow path pattern other than mixing.

BEST MODE FOR CARRYING OUT THE INVENTION

Referring to FIGS. 1 to 22A and 22B, the following will describe an embodiment of a device for analysis and an analyzing apparatus and method using the device according to the present invention.

Figure 1:
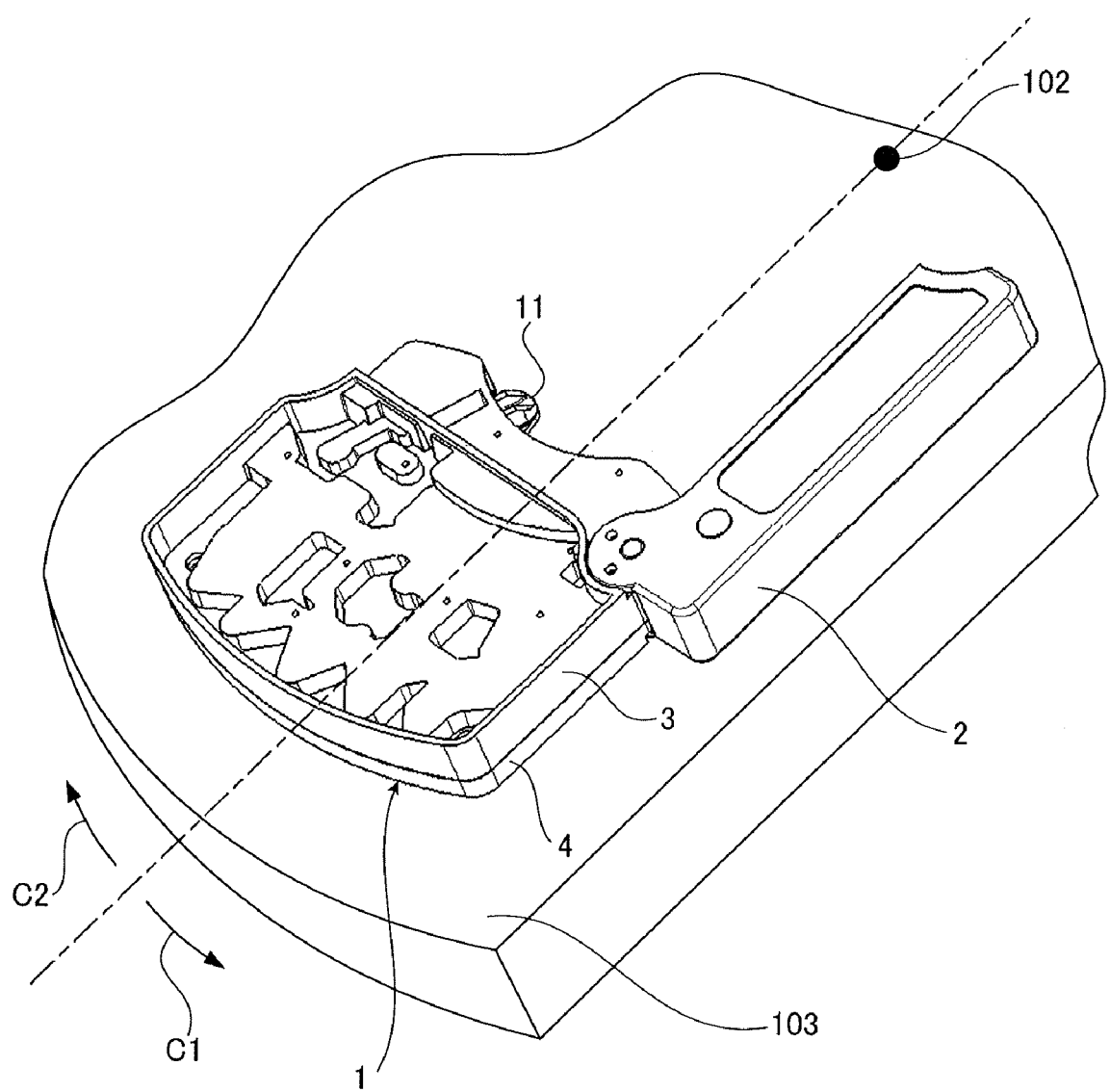
FIG. 1 is a main part perspective view showing a device for analysis set in an analyzing apparatus according to an embodiment of the present invention.
Figure 2:
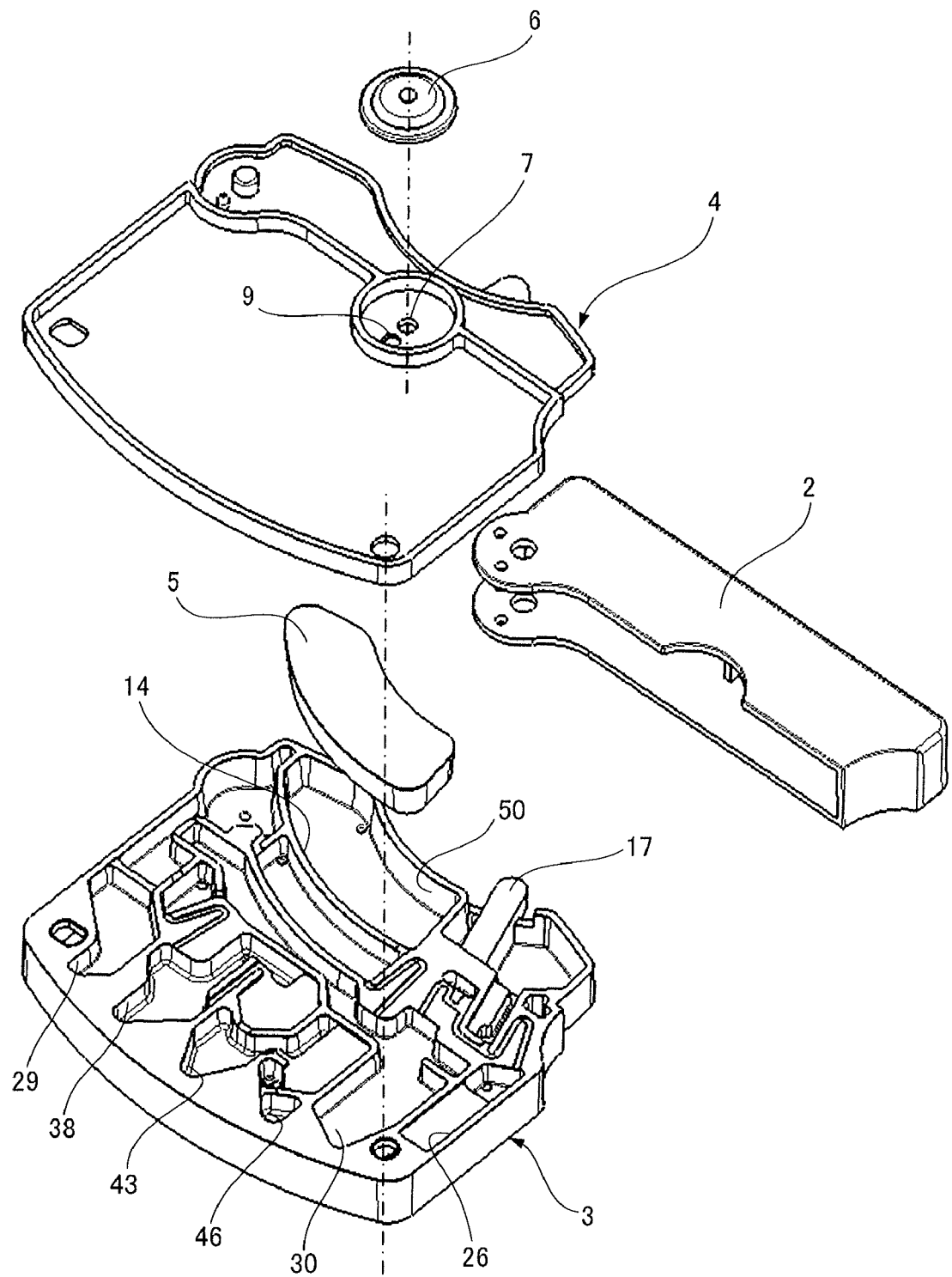
FIG. 2 is an exploded perspective view showing the device for analysis according to the embodiment.

FIG. 1 shows that a device for analysis 1 is set on a rotor 103 of the analyzing apparatus according to the embodiment of the present invention. FIG. 2 shows that the device for analysis 1 is disassembled such that a surface in contact with the rotor 103 is placed face up.

The device for analysis 1 is made up of five components of a protective cap 2 for preventing the scattering of a sample solution, a base substrate 3 on which a micro channel structure having minute asperities thereon is formed, a cover substrate 4 covering the surface of the base substrate 3, a diluting unit 5 for retaining a diluent, and an opening button 6 for discharging the diluent in the diluting unit 5 set on a recessed portion 50 out of several recessed portions formed on the top surface of the base substrate 3.

The base substrate 3 and the cover substrate 4 are joined to each other with the diluting unit 5 and the like set therein, and the protective cap 2 is attached to the joined substrates. Further, the opening button 6 is joined while being centered at the position of an opening hole 7 formed on the cover substrate 4.

The openings of the several recessed portions formed on the top surface of the base substrate 3 are covered with the cover substrate 4, thereby forming a plurality of storage areas which will be described later (like measurement spots which will be described later) and flow paths and the like connecting the storage areas (see FIG. 2). Reagents necessary for various analyses are stored beforehand in necessary ones of the storage areas.

The device for analysis 1 can collect a sample solution, for example, a solution such as blood from an inlet 11. By setting the device for analysis 1 on the rotor 103 of the analyzing apparatus with the protective cap 2 closed, the components of the sample solution can be analyzed. Reference numeral 102 denotes the axis of rotation of the rotor 103.

By using a centrifugal force generated by rotating the device for analysis 1 about the axis 102 disposed inside the inlet 11 and a capillary force of a capillary flow path provided in the device for analysis 1, the device for analysis 1 transfers the sample solution therein, the sample solution having been collected into the device for analysis 1 from the inlet 11. The protective cap 2 is attached to prevent the sample solution having adhered around the inlet 11 from being scattered to the outside by a centrifugal force during an analysis.

The components constituting the device for analysis 1 of the present invention are desirably made of resin materials which can reduce the manufacturing cost with high mass productivity. The analyzing apparatus analyzes the sample solution by an optical measurement method in which light passing through the device for analysis 1 is measured. Thus the base substrate 3 and the cover substrate 4 are desirably made of resins such as PC, PMMA, AS, and MS which have high transparency.

Further, the diluting unit 5 is desirably made of a crystalline resin such as PP and PE which have low moisture permeabilities because the diluent has to be contained in the diluting unit 5 for a long period of time. The opening button 6 is desirably made of a crystalline resin such as PP having a high modulus of elasticity because the opening button 6 is deformed when the diluting unit 5 is opened. The protective cap 2 is desirably made of an inexpensive resin such as PP and PE, and may be made of any materials as long as high moldability is obtained.

The base substrate 3 and the cover substrate 4 are desirably joined by a method hardly affecting the reaction activity of the reagent stored in the storage area. Ultrasonic welding and laser welding are desirable in which reactive gas and a reactive solvent are hardly generated upon joining.

On a part where a solution is transferred by a capillary force which is generated through a small clearance between the substrates 3 and 4 by the joining of the base substrate 3 and the cover substrate 4, hydrophilization is performed to increase the capillary force. To be specific, hydrophilization is performed using a hydrophilic polymer, a surface-active agent, and so on. In this case, hydrophilicity is a state in which a contact angle with water is less than 90°. A contact angle of less than 40° is more preferable.

FIGS. 3 to 6A, 6B, and 6C show the analyzing apparatus in which the device for analysis 1 is set.

Figure 3:
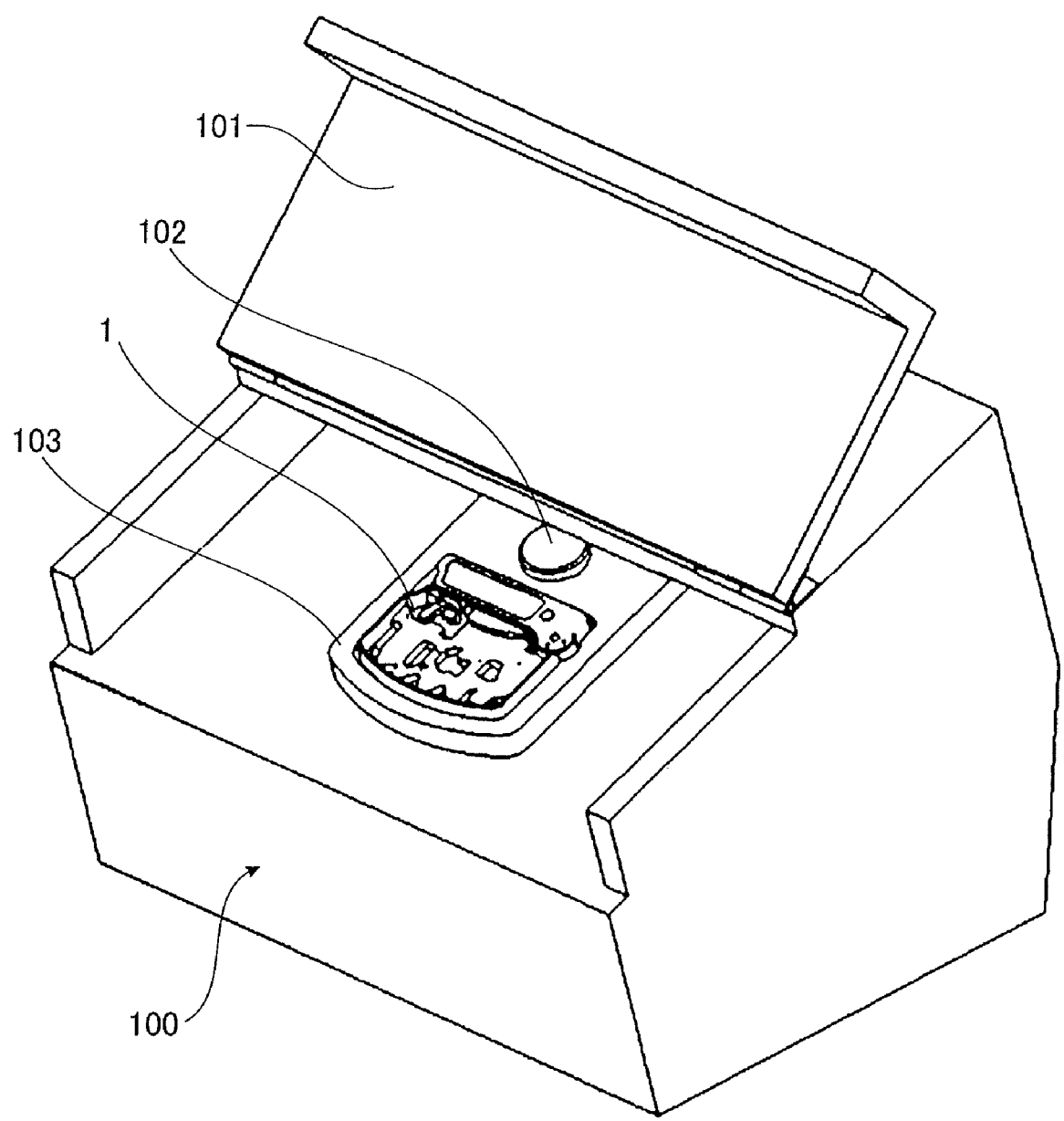
FIG. 3 is an outside drawing showing the analyzing apparatus according to the embodiment.

In FIG. 3, the device for analysis 1 is placed on the rotor 103, which rotates about the axis 102 of the analyzing apparatus 100, with the cover substrate 4 placed under the base substrate 3, and an analysis is conducted with a lid 101 closed.

Figure 4:
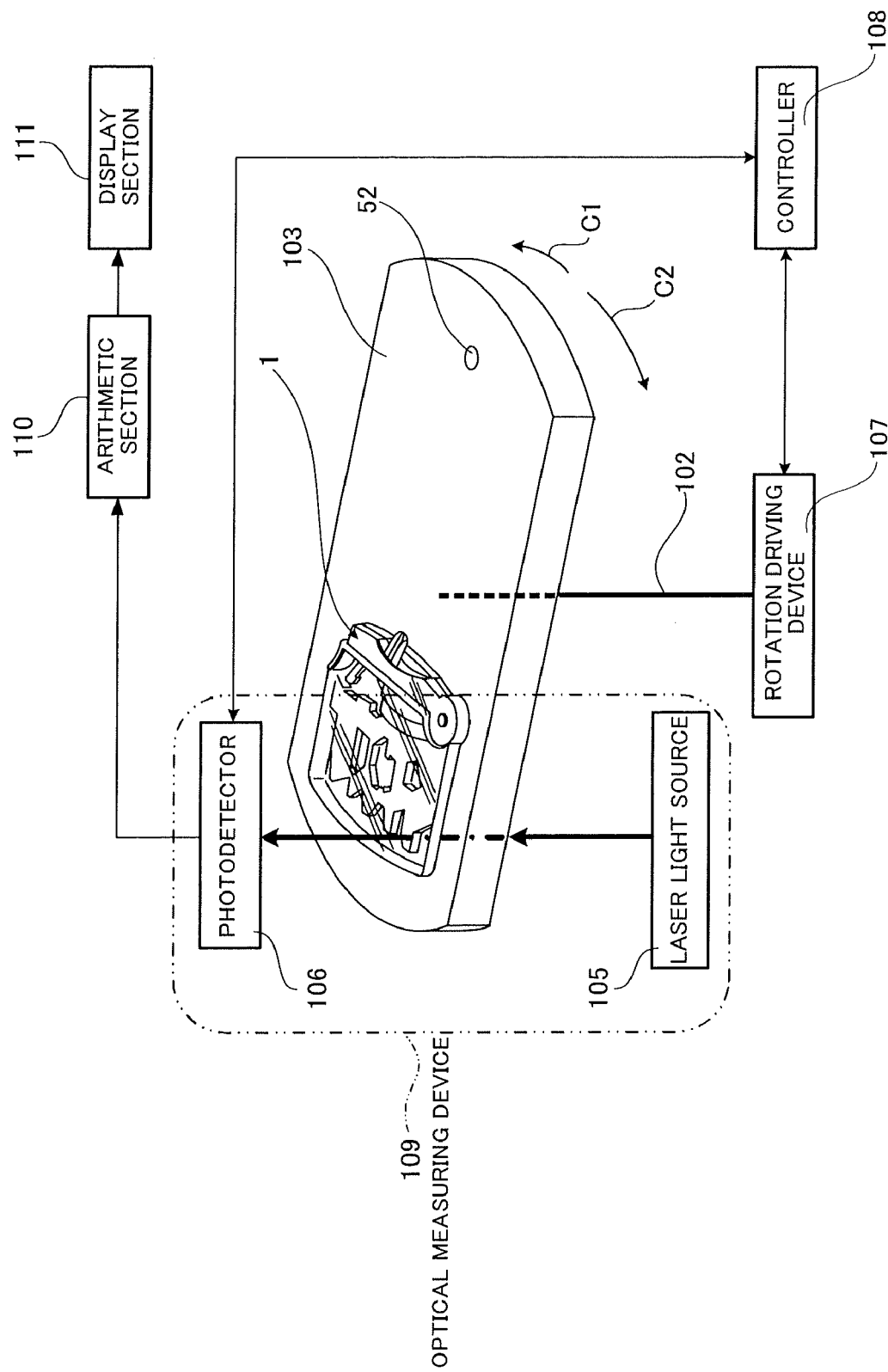
FIG. 4 is a structural diagram showing the analyzing apparatus according to the embodiment.
Figure 5:
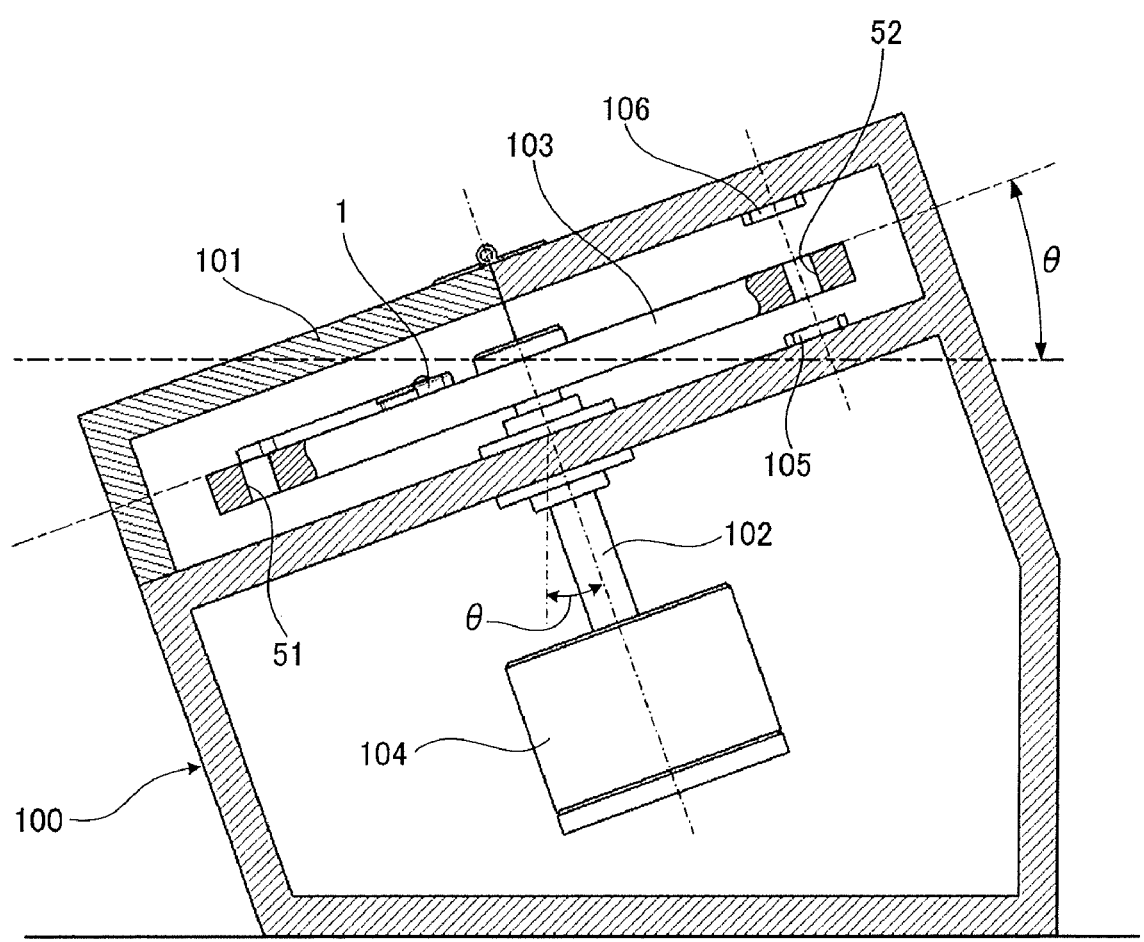
FIG. 5 is a sectional view showing the analyzing apparatus according to the embodiment.

As shown in FIGS. 4 and 5, the analyzing apparatus 100 is made up of a rotation driving device 107 for rotating the rotor 103, an optical measuring device 109 for optically measuring the solution in the device for analysis 1, a controller 108 for controlling the rotation speed and rotation direction of the rotor 103 and the measurement timing and so on of the optical measuring device, an arithmetic section 110 for processing a signal obtained by the optical measuring device 109 and computing a measurement result, and a display section 111 for displaying the result obtained by the arithmetic section 110.

The rotation driving device 107 rotates the device for analysis 1 about the axis 102 in any direction at a predetermined rotation speed through the rotor 103 and the rotation driving device 107 further laterally reciprocates the device for analysis 1 at a predetermined stop position about the axis 102 over a predetermined amplitude range and period, so that the device for analysis 1 can be swung. In this configuration, a motor 104 is used as the rotation driving device 107 to rotate the rotor 103 about the axis 102. The axis 102 is inclined only by an angle of inclination of θ° relative to a predetermined position on the axis 102 and is rotatably mounted.

In this configuration, the device for analysis 1 is rotated and swung by the single rotation driving device 107. Another driving device for swinging may be provided to reduce the load of the rotation driving device 107. To be specific, a vibrator such as a vibration motor prepared in addition to the motor 104 is brought into direct or indirect contact with the device for analysis 1 set on the rotor 103, so that the device for analysis 1 is swung to apply an inertial force to the solution in the device for analysis 1.

The optical measuring device 109 includes a laser light source 105 for irradiating the measurement part of the device for analysis 1 with laser light and a photodetector 106 for detecting the quantity of light transmitted through the device for analysis 1 out of the laser light emitted from the laser light source 105. When the rotor 103 is made of a material having low translucency or a material having no translucency, holes 51 and 52 are drilled at the mounting positions of the device for analysis 1 on the rotor 103.

In this configuration, the laser light source 105 is capable of switching the waveforms of outgoing light and the photodetector 106 is capable of detecting light of any waveforms from the outgoing light of the laser light source 105.

Further, multiple pairs of the laser light sources 105 and the photodetectors 106 may be provided according to the number of waveforms necessary for measurement.

The analyzing apparatus 100 may have a mechanism in which an opening device is provided for automatically opening the diluting unit 5 in the device for analysis 1, to be specific, an arm enabling a vertical motion is provided on the rotor 103 to operate the opening button 6 of the device for analysis 1 set on the rotor 103 and the opening button 6 is lifted by the arm.

As shown in FIG. 5, the rotor 103 is attached to the inclined axis 102 and is inclined by the angle of inclination of θ° relative to a horizontal line, and the rotor 103 can control the direction of gravity applied to the solution in the device for analysis 1 according to the rotation stop position of the device for analysis 1.

Figure 6A:
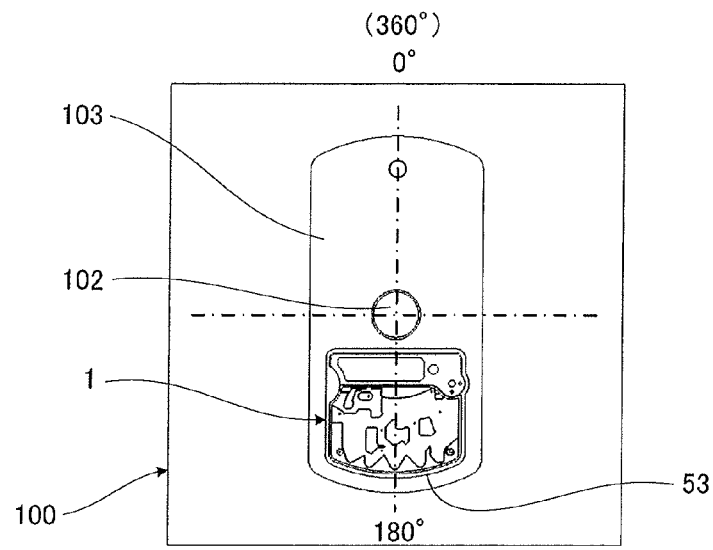
FIG. 6A shows a rotation stop position of the device for analysis according to the embodiment.

To be specific, when the device for analysis 1 is stopped at a position shown in FIG. 6A (a position at around 180° when a point immediately above is expressed as 0° (360°)), a lower side 53 of the device for analysis 1 is directed downward when viewed from the front, so that a force of gravity is applied to the solution in the device for analysis 1 toward the outer periphery (the lower side 53).

Figure 6B:
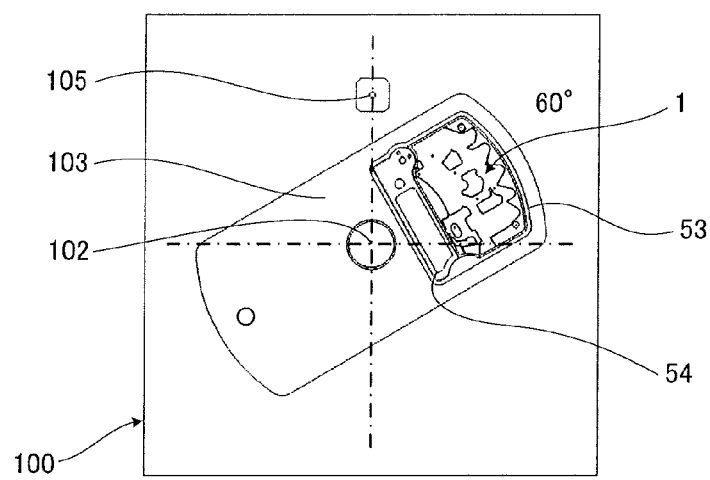
FIG. 6B shows a rotation stop position of the device for analysis according to the embodiment.
Figure 6C:
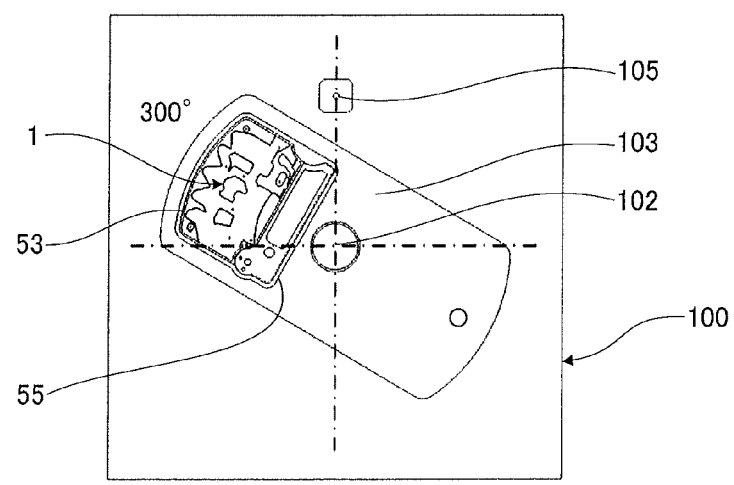
FIG. 6C shows a rotation stop position of the device for analysis according to the embodiment.

When the device for analysis 1 is stopped at a position around 60° as shown in FIG. 6B, an upper left side 54 of the device for analysis 1 is directed downward when viewed from the front, so that a force of gravity is applied to the solution in the device for analysis 1 toward the upper left. Similarly, at a position around 300° in FIG. 6C, an upper right side 55 of the device for analysis 1 is directed downward when viewed from the front, so that a force of gravity is applied to the solution in the device for analysis 1 toward the upper right.

The axis 102 is inclined and the device for analysis 1 is stopped at any one of the positions, so that the force of gravity can be used as one of driving forces for transferring the solution in the device for analysis 1 in a predetermined direction.

The force of gravity applied to the solution in the device for analysis 1 can be set by adjusting the angle of inclination θ of the axis 102 and is desirably set according to the relationship between an amount of liquid to be transferred and an adhesion force on a wall surface in the device for analysis 1.

The angle of inclination θ is desirably set at 10° to 45°. When the angle of inclination θ is smaller than 10°, the force of gravity applied to the solution is too small and a driving force necessary for transfer may not be obtained. When the angle of inclination θ is larger than 45°, a load applied to the axis 102 may increase or the solution transferred by a centrifugal force may be moved by the self weight in an uncontrolled manner.

In the analyzing apparatus 100 of the present embodiment, the angle of inclination θ is fixed at any angle ranging from 10° to 45° and the motor 104 acting as the rotation driving device 107, the laser light source 105, and the photodetector 106 are also mounted in parallel with the inclined axis 102. The angle of inclination θ can be adjusted to any angle and the angles of the motor 104, the laser light source 105, and the photodetector 106 can be also changed accordingly, so that the optimum angle of inclination can be set according to the specification of the device for analysis 1 and a transfer process in the device for analysis 1. In the configuration where the angle of inclination θ can be adjusted to any angle, the angle of inclination θ is desirably set at 0° to 45°. In order to eliminate the influence of the force of gravity, the rotor 103 can be rotated with the angle of inclination of 0°, that is, in a horizontal position.

FIGS. 7A and 7B to 13 show the detail of the device for analysis 1.

Figure 7A:
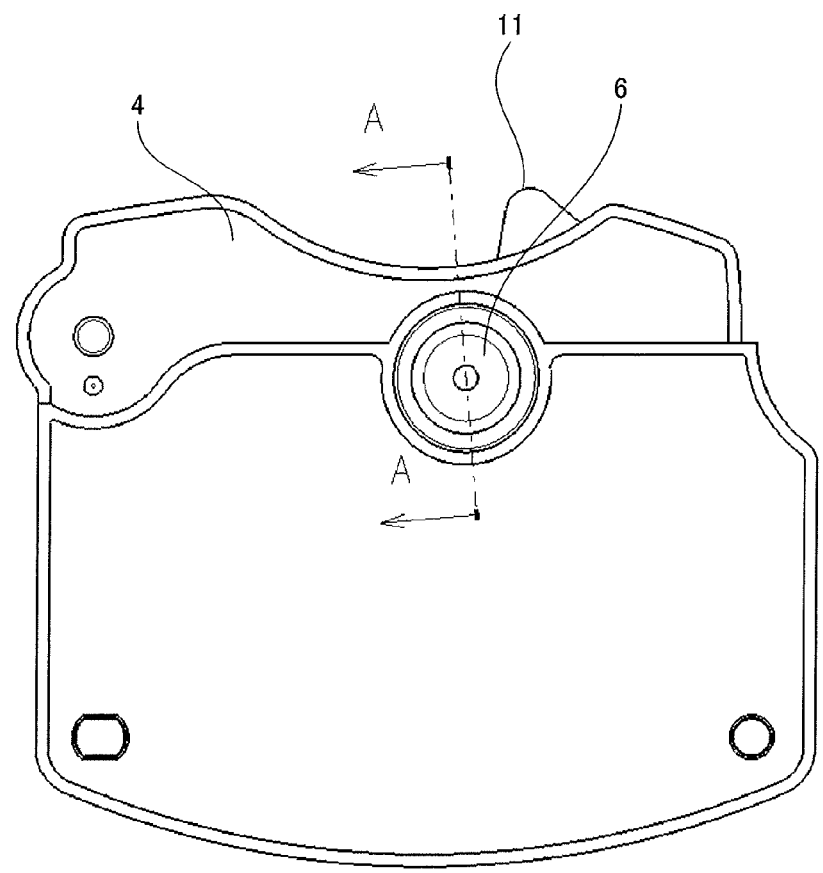
FIG. 7A is a plan view showing the opening part of the diluting unit of the device for analysis according to the embodiment.
Figure 7B:
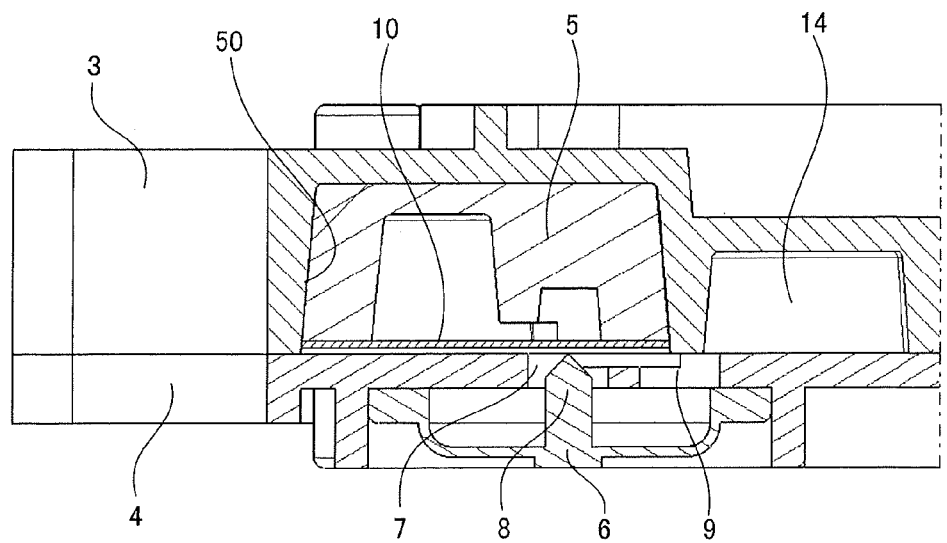
FIG. 7B is a sectional view showing the opening part of the diluting unit of the device for analysis according to the embodiment.

FIGS. 7A and 7B show the opening part of the diluting unit of the device for analysis 1.

FIG. 7A is a plan view showing a position where the opening button 6 is attached. FIG. 7B is a sectional view taken along line A-A of FIG. 7A.

When the diluting unit 5 is opened and the diluent is discharged, the center of the opening button 6 joined to the cover substrate 4 as shown in FIG. 7B is pressed from below, so that a pin 8 penetrates an aluminum seal 10 bonded to a surface of the diluting unit 5 and the diluting unit 5 is opened. After that, when the device for analysis 1 is rotated with the opened diluting unit 5, the diluent in the diluting unit 5 is discharged to a retaining cavity 14, which serves as a second retaining section, through a space formed between the opening hole 7 and a discharge hole 9 (a discharge groove formed between the base substrate 3 and the cover substrate 4 and a space formed between the cover substrate 4 and the opening button 6).

Figure 8A:
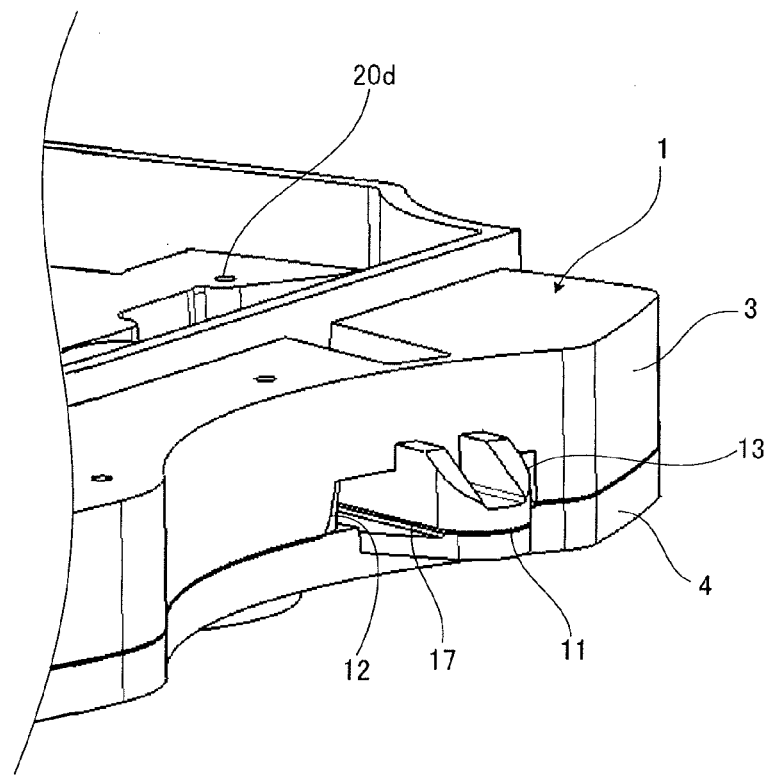
FIG. 8A is an enlarged perspective view around the inlet of the device for analysis according to the embodiment.
Figure 8B:
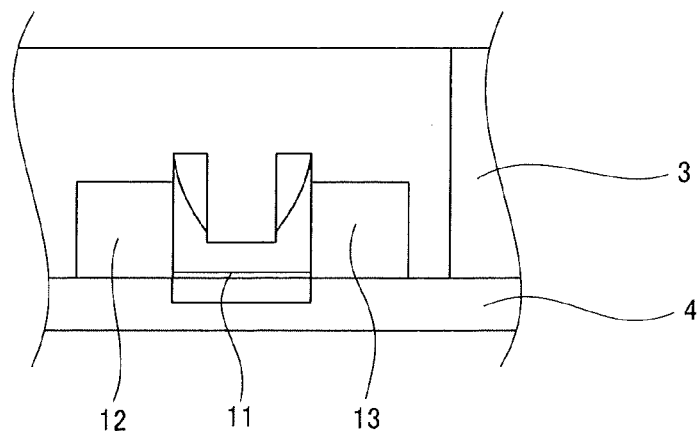
FIG. 8B is a front view around the inlet of the device for analysis according to the embodiment.
Figure 9:
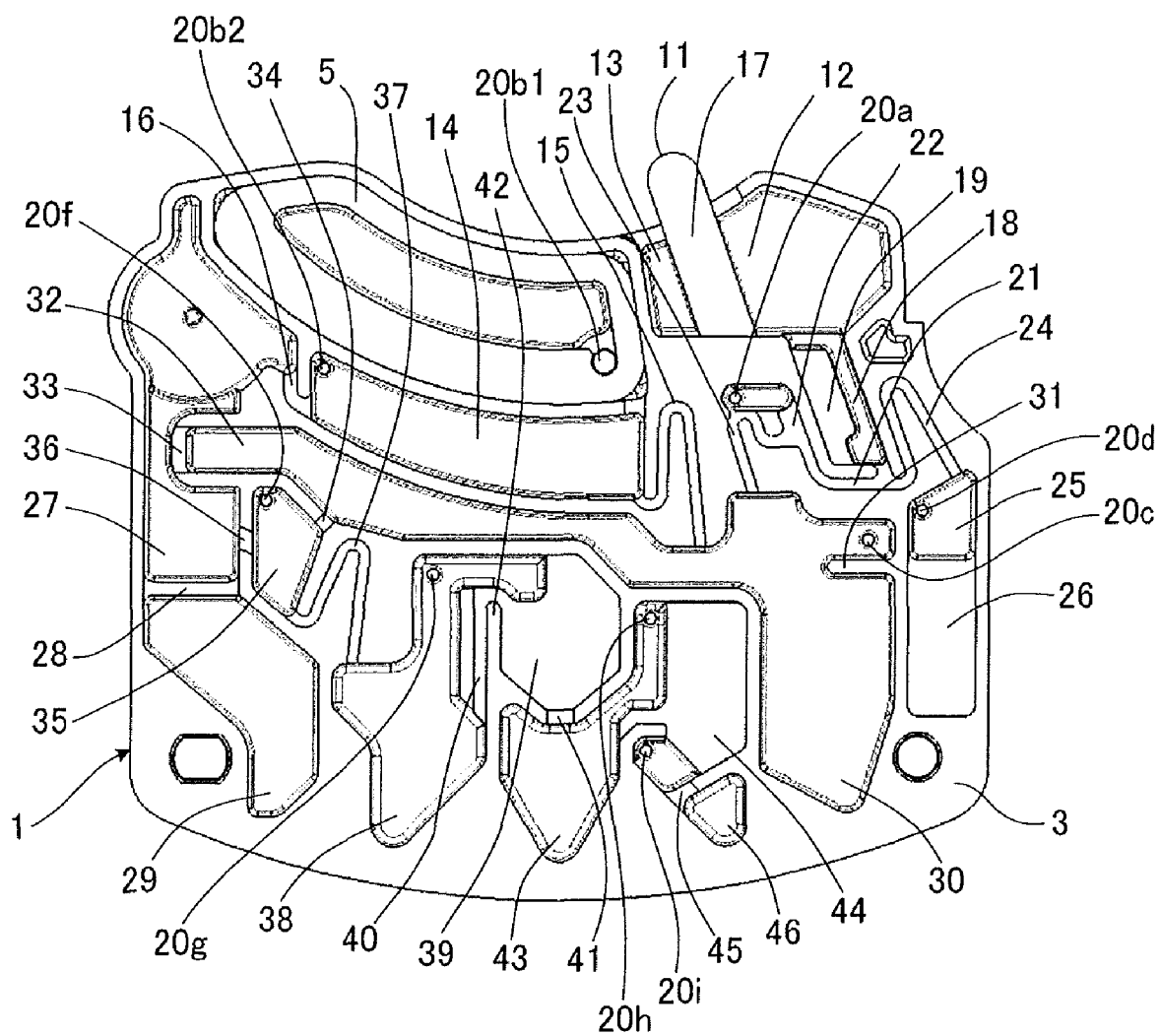
FIG. 9 is a plan view showing the micro channel structure of the device for analysis according to the embodiment.

FIG. 8A is an enlarged perspective view around the inlet of the device for analysis 1. FIG. 8B is a front view of FIG. 8A. FIG. 9 is a plan view of the faying surface of the base substrate 3, which is shown in FIG. 2, with the cover substrate 4.

In the device for analysis 1, the sample solution is caused to adhere to the inlet 11, so that the sample solution can be sucked by the capillary force of a capillary cavity 17 formed in the inlet 11. Thus blood can be directly collected from a fingertip and so on. In this configuration, the inlet 11 protrudes along the axis 102 from one side of the body of the device for analysis 1 and thus prevents blood of a finger and so on from coming into contact with a location other than the inlet 11, thereby preventing blood having adhered during analysis from scattering to the outside.

On one side of the capillary cavity 17, cavities 12 and 13 are provided which have larger cross-sectional dimensions than the capillary cavity 17 in the thickness direction and communicate with the atmosphere. Since the cavities 12 and 13 are provided, the sample solution passing through the capillary cavity 17 is not a capillary flow first flowing from a side but a capillary flow first flowing from the center. Thus even when the sample solution is charged in multiple times, a sample solution retained in the capillary cavity 17 and a sample solution collected later come into contact with each other first from the centers. Further, the sample solutions are charged while air in the capillary cavity 17 is discharged to the cavities 12 and 13 disposed on the sides of the capillary cavity 17. Thus even when an amount of the sample solution to be adhered to the inlet 11 is found to be insufficient during collection or even when a fingertip is separated from the inlet 11 during collection, the collection can be repeated until the sample solution is fully collected into the capillary cavity 17. In this configuration, the capillary cavity 17 has a cross-sectional dimension of 50 μm to 300 μm in the thickness direction and the cavities 12 and 13 have cross-sectional dimensions of 1000 μm to 3000 μm in the thickness direction. The dimension of the capillary cavity 17 is not particularly limited as long as the sample solution can be collected by a capillary force, and the dimensions of the cavities 12 and 13 are not particularly limited as long as the sample solution is not transferred by a capillary force.

Figure 10:
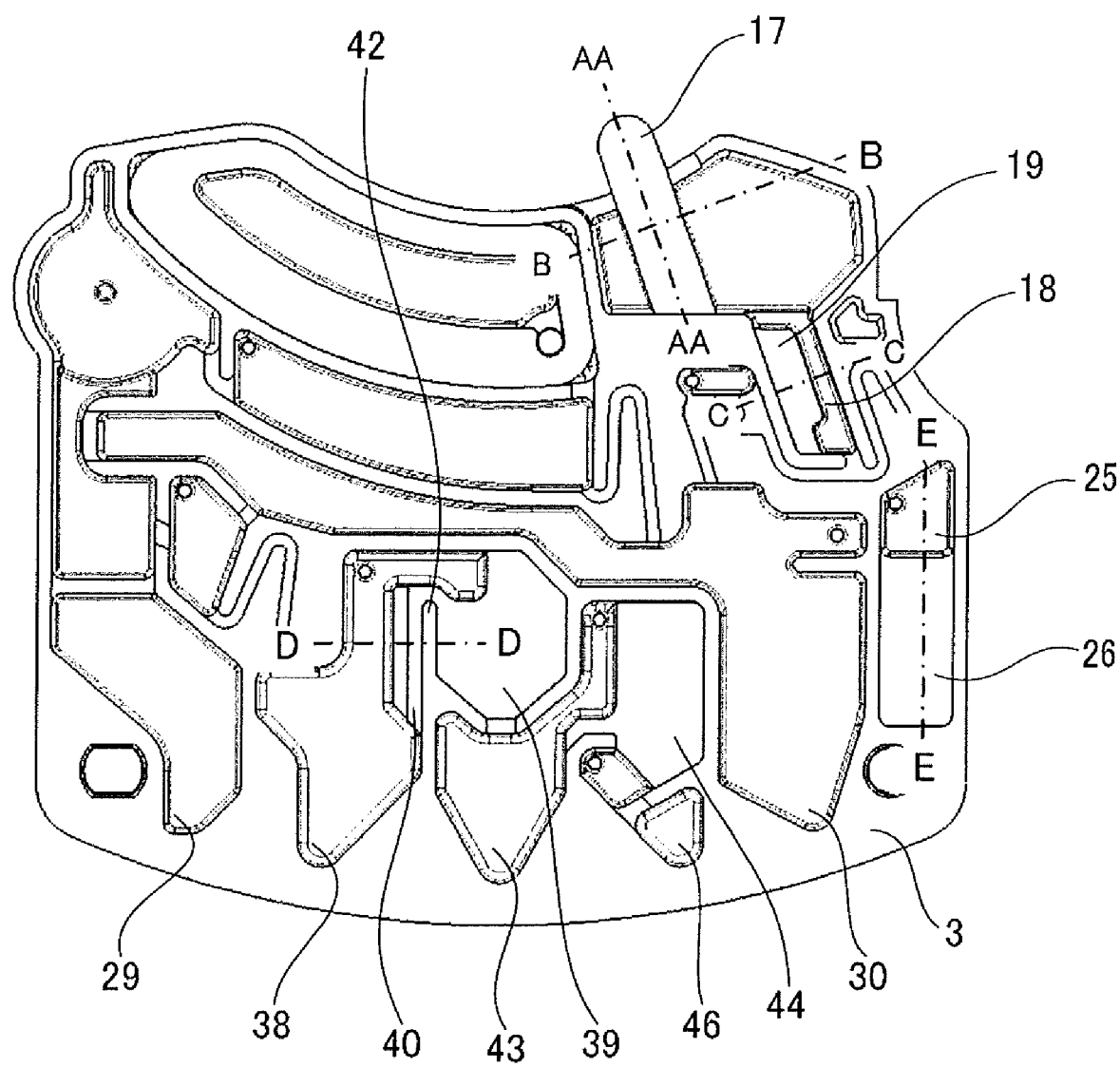
FIG. 10 is a plan view showing the sectional position of the device for analysis according to the embodiment.
Figure 11A:
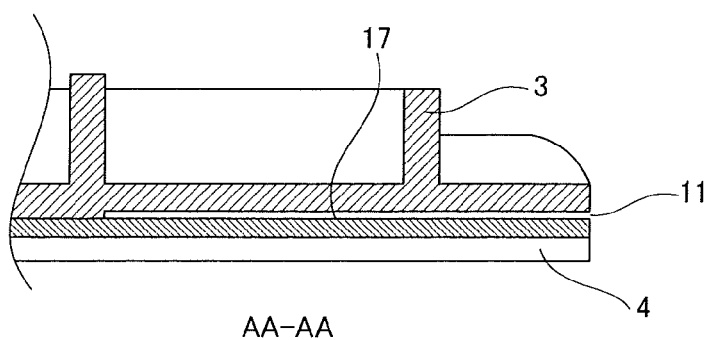
FIG. 11A is a sectional view showing the device for analysis taken along line AA-AA according to the embodiment.
Figure 11B:
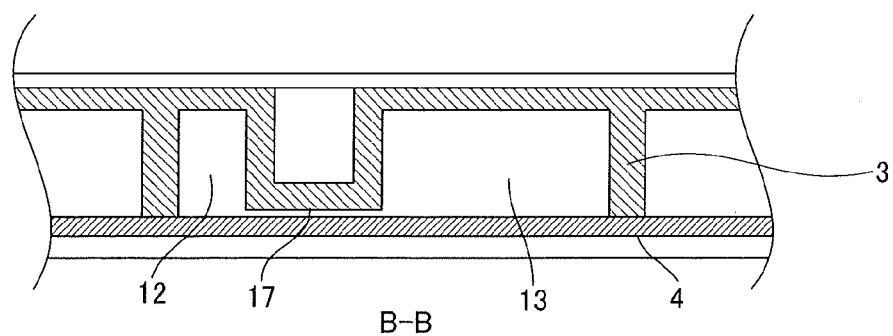
FIG. 11B is a sectional view showing the device for analysis taken along line B-B according to the embodiment.
Figure 11C:
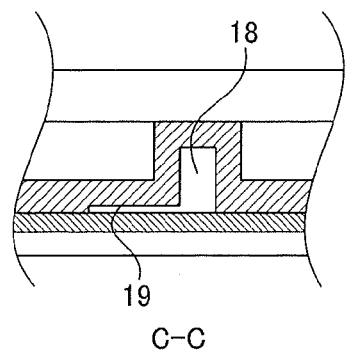
FIG. 11C is a sectional view showing the device for analysis taken along line C-C according to the embodiment.
Figure 11D:
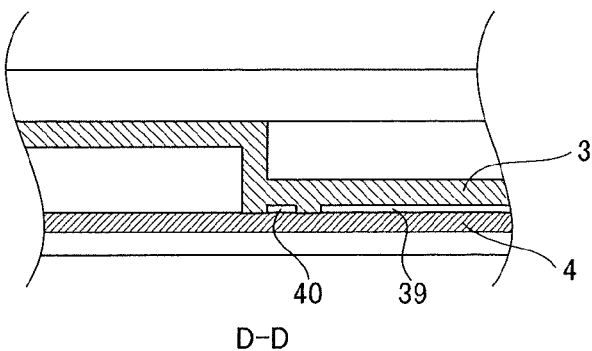
FIG. 11D is a sectional view showing the device for analysis taken along line D-D according to the embodiment.
Figure 11E:
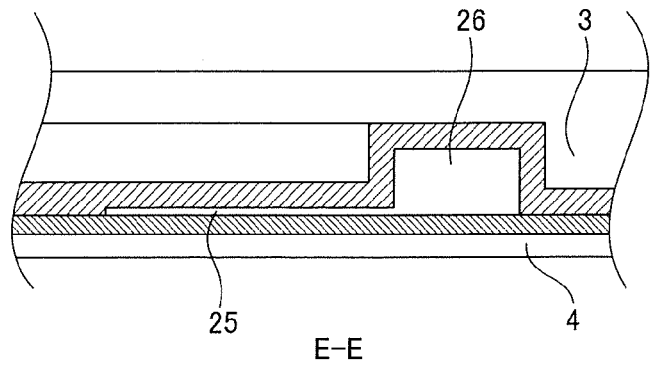
FIG. 11E is a sectional view showing the device for analysis taken along line E-E according to the embodiment.
Figure 12:
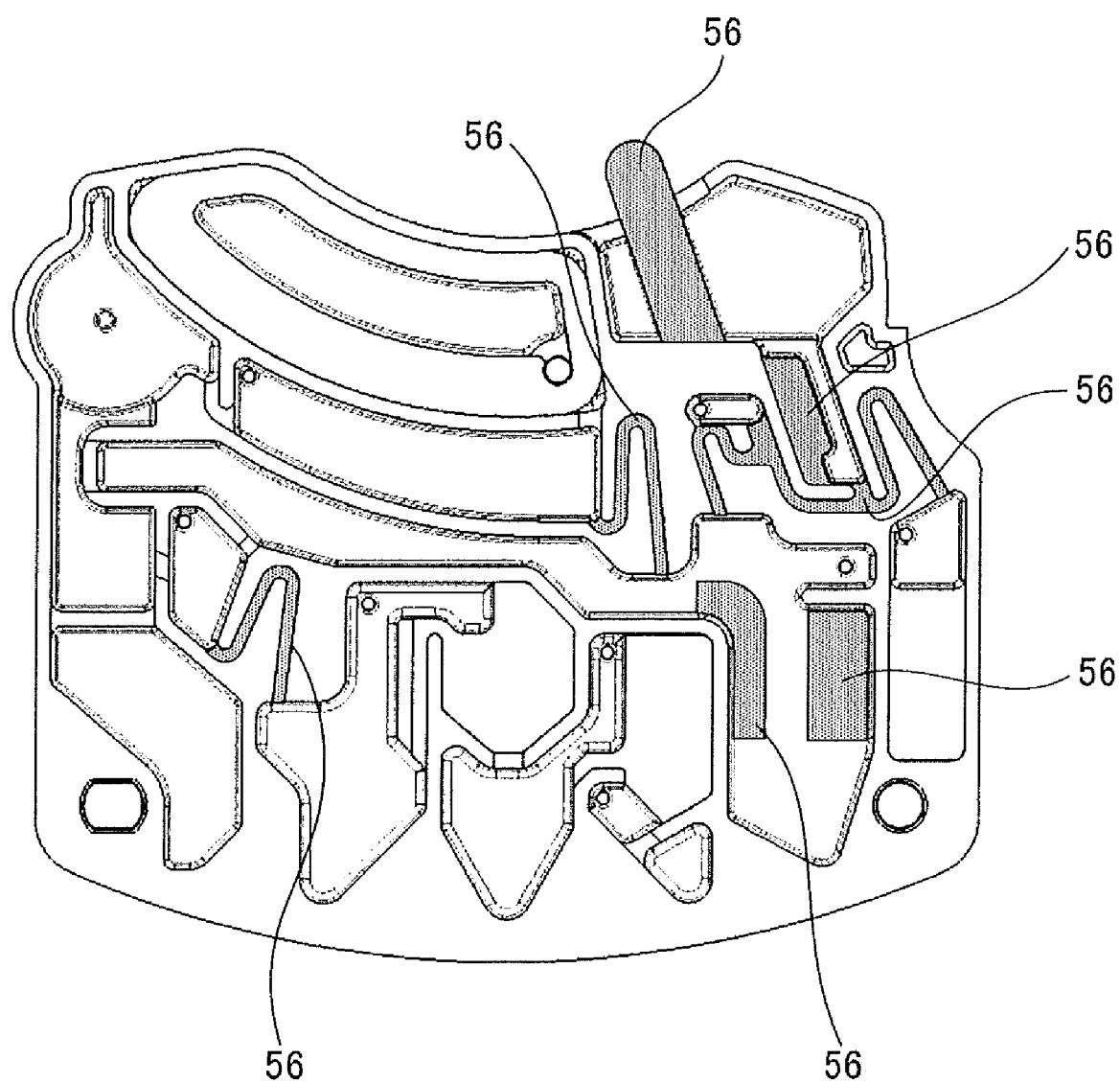
FIG. 12 is a plan view showing the hydrophilized locations of the device for analysis according to the embodiment.

FIGS. 11A to 11E are enlarged sectional views taken along lines AA-AA, B-B, C-C, D-D, and E-E of FIG. 10. Reference characters 20*a*, 20*b*1, 20*b*2, 20*c*, 20*d*, 20*e*, 20*f*, 20*g*, 20*h*, and 20*i* denote air holes. FIG. 12 shows hydrophilized locations by hatching.

The following will specifically describe the micro channel structure of the device for analysis and the transfer process of the solution according to a first embodiment of the present invention.

Figure 13:
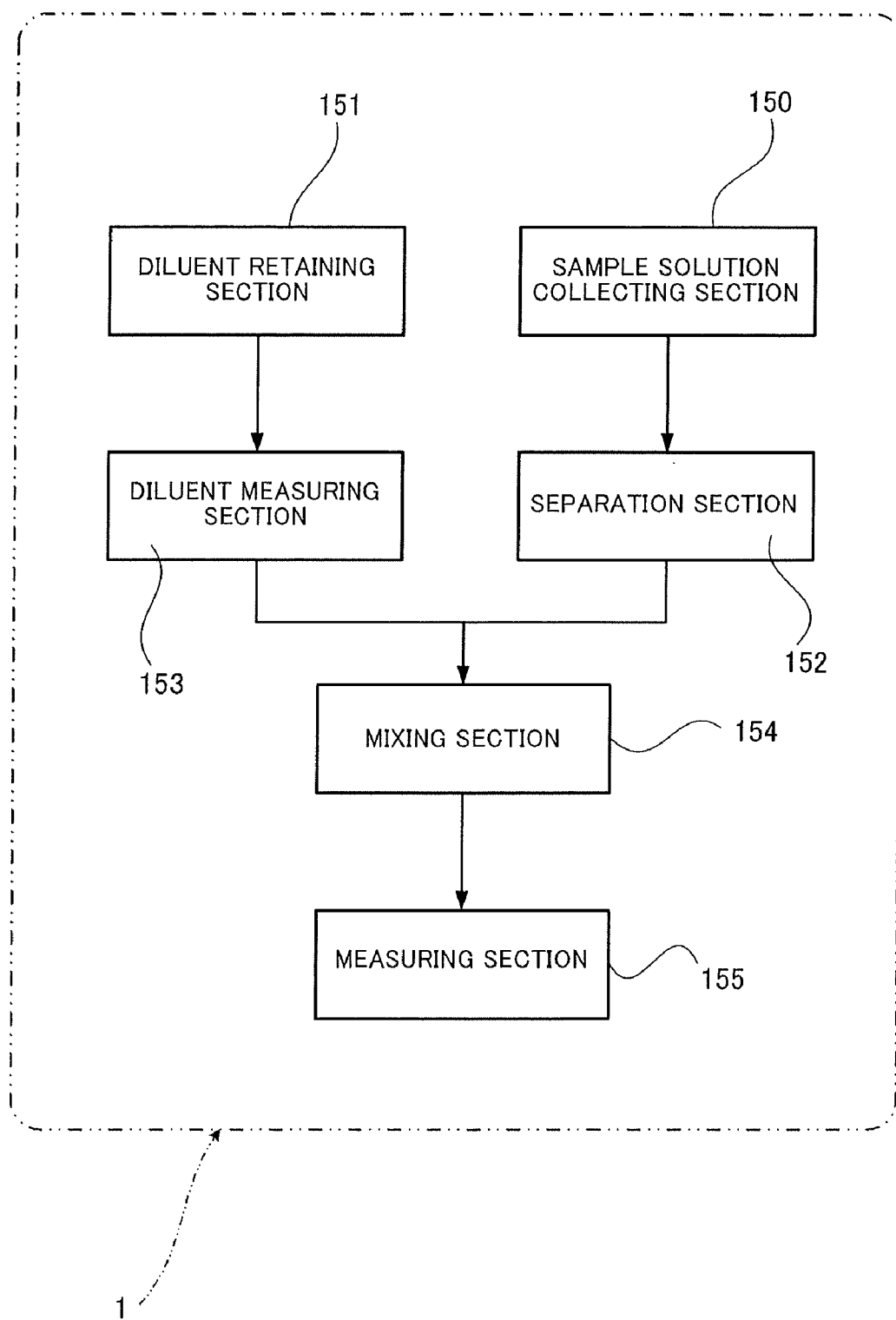
FIG. 13 is a structural diagram showing the device for analysis according to the embodiment.

FIG. 13 is a block diagram showing the configuration of the device for analysis 1. In the device for analysis 1, a sample solution collecting section 150 is formed for collecting a sample solution, a diluent retaining section 151 is formed for retaining a diluent for diluting the sample solution, a separation section 152 is formed for retaining the sample solution transferred from the sample solution collecting section 150, centrifuging the sample solution into solution constituents and solid constituents, and then collecting the sample solution containing a predetermined amount of the solid constituents, a diluent measuring section 153 is formed for measuring the diluent transferred from the diluent retaining section 151, a mixing section 154 is formed for retaining the sample solution transferred from the separation section 152 and the diluent transferred from the diluent measuring section 153, mixing the solutions therein, and then measuring the diluted solution to obtain an amount for analysis, and a measuring section 155 is formed for reacting the diluted solution transferred from the mixing section 154 with an analytical reagent and measuring the solution.

As shown in FIG. 9, the sample solution collecting section 150 is made up of the inlet 11 for collecting the sample solution, the capillary cavity 17 for collecting the sample solution through the inlet 11 by a capillary force and retaining a specified amount of the sample solution, and the cavities 12 and 13 for discharging air in the capillary cavity 17 during the collection of the sample solution.

As shown in FIG. 9, the diluent retaining section 151 has the diluent retained in the diluting unit 5. The diluent is spread by the opening operation illustrated in FIGS. 7A and 7B.

The separation section 152 on the downstream side of the sample solution collecting section 150 is made up of, as shown in FIG. 9, a separation cavity 18 which is formed so as to communicate with the capillary cavity 17 through the cavity 12, retains the sample solution transferred from the capillary cavity 17 by a centrifugal force, and separates the sample solution into solution constituents and solid constituents by the centrifugal force, a measurement flow path 23 which is formed between the separation cavity 18 and the diluent measuring section 153 and acts as a first retaining part for retaining transferred constituents of the solid constituents having been separated by the separation cavity 18, a connection flow path 21 for connecting the measurement flow path 23 and the separation cavity 18 to transfer the sample solution in the separation cavity 18, an overflow path 22 which is formed between the separation cavity 18 and the diluent measuring section 153 to preferentially retain the solution constituents of the sample solution having been separated in the connection flow path 21 and transfer only the solid constituents into the measurement flow path 23, a capillary cavity 19 which is formed in the separation cavity 18 to suppress the transfer of the separated solution constituents in the separation cavity 18 to the measurement flow path 23, a connection flow path 24 which is formed on the opposite side of the separation cavity 18 from the measurement flow path 23 to discharge a sample solution unnecessary for analysis in the separation cavity 18, the connection flow path 21, and the overflow path 22, and overflow cavities 25 and 26 for retaining the unnecessary sample solution transferred through the connection flow path 24.

In this configuration, the connection flow path 21, the overflow path 22, the measurement flow path 23, the connection flow path 24, the capillary cavity 19, and the overflow cavity 26 are 50 μm to 300 μm in cross-sectional dimension in the thickness direction. The dimensions are not particularly limited as long as the sample solution can be transferred by a capillary force. Further, the separation cavity 18 and the overflow cavity 25 are 1000 μm to 3000 μm in cross-sectional dimension in the thickness direction. The dimensions can be adjusted according to a necessary amount of the sample solution.

The diluent measuring section 153 formed on the downstream side of the diluent retaining section 151 is made up of, as shown in FIG. 9, the retaining cavity 14 for retaining only a specified amount of the diluent transferred from the diluting unit 5 by a centrifugal force, a connection flow path 15 which is formed between the retaining cavity 14 and the separation section 152 to transfer to the mixing section 154 the diluent having been measured in the retaining cavity 14, an overflow path 16 which is formed on the opposite side of the retaining cavity 14 from the connection flow path 15 to cause the diluent to overflow outside the retaining cavity 14 when the diluent transferred to the retaining cavity 14 exceeds a predetermined amount, an overflow cavity 27 which specifies the liquid level of the solution retained in the retaining cavity 14 and allows the diluent to overflow through the overflow path 16, a measurement spot 29 which retains the overflowing diluent and is used for the reference measurement of the optical measuring device 109, and a capillary portion 28 for preventing the diluent retained in the measurement spot 29 from flowing backward into another area.

In this configuration, the connection flow path 15, the overflow path 16, and the capillary portion 28 are 50 μm to 300 μm in cross-sectional dimension in the thickness direction. The dimensions are not particularly limited as long as a capillary force is applied. Moreover, the retaining cavity 14, the overflow cavity 27, and the measurement spot 29 are 1000 μm to 3000 μm in cross-sectional dimension in the thickness direction. The dimensions can be adjusted according to conditions (including an optical path length and a measured wavelength) for measuring a required amount of the sample solution and an absorbance.

The mixing section 154 on the downstream side of the separation section 152 and the diluent measuring section 153 is made up of, as shown in FIG. 9, an operation cavity 30 acting as a third retaining section which is formed so as to communicate with the measurement flow path 23 and the connection flow path 15, retains the sample solution transferred from the measurement flow path 23 and the diluent transferred from the retaining cavity 14, and mix the solutions therein, a rib 31 formed to prevent the diluted solution from flowing during mixing from the air hole 20c provided in the operation cavity 30, a retaining cavity 32 acting as a fourth retaining section which is formed inside the liquid level of the diluted solution retained in the operation cavity 30, relative to the direction of the axis 102, and retains the diluted solution mixed and transferred from the operation cavity 30, a retaining cavity 35 which is formed on the downstream side of the retaining cavity 32 to retain only a specific amount of the diluted solution transferred from the retaining cavity 32 by a centrifugal force, a capillary portion 33 which is formed between the retaining cavity 32 and the overflow cavity 27 to prevent the diluted solution transferred to the retaining cavity 32 from flowing into the overflow cavity 27, a connection flow path 34 which is formed between the retaining cavity 32 and the retaining cavity 35 to prevent the diluted solution transferred to the retaining cavity 32 from flowing into the retaining cavity 35, a connection flow path 37 which is formed between the retaining cavity 35 and the measuring section 155 located downstream from the retaining cavity 35 and transfers the diluted solution having been measured by the retaining cavity 35 to the measuring section 155, and an overflow path 36 which is formed between the retaining cavity 35 and the overflow cavity 27 to cause the diluted solution to overflow outside the retaining cavity 35 when the diluent transferred to the retaining cavity 35 exceeds a predetermined amount.

In this configuration, the capillary portion 33, the connection flow path 34, the overflow path 36, and the connection flow path 37 are 50 μm to 300 μm in cross-sectional dimension in the thickness direction. The dimensions are not particularly limited as long as a capillary force is applied. Moreover, the retaining cavity 32 and the retaining cavity 35 are 1000 μm to 3000 μm in cross-sectional dimension in the thickness direction. The dimensions can be adjusted according to a required amount of the diluted solution.

The measuring section 155 on the downstream side of the mixing section 154 is made up of, as shown in FIG. 9, a measurement spot 38 which is formed so as to communicate with the retaining cavity 35 through the connection flow path 37, reacts the reagent stored in the measurement spot 38 and the diluted solution transferred from the retaining cavity 35 through the connection flow path 37, retains the solution after the reaction, and conducts a first measurement, a capillary cavity 39 which is formed inside, relative to the direction of the axis 102 when viewed from a measurement spot 43, the liquid level of a first reaction liquid retained in the measurement spot 38 acting as an operation cavity and acts as a receiving cavity for collecting the first reaction liquid in the measurement spot 38 after the first reaction liquid is measured, a capillary cavity 40 which is formed between the measurement spot 38 and the capillary cavity 39 to stabilize the amount of the first reaction liquid returning to the measurement spot 38, a connection flow path 41 which is formed downstream from the capillary cavity 39 to prevent the first reaction liquid collected in the capillary cavity 39 from flowing into the measurement spot 43, a rib 42 which is located at a connection section between the capillary cavity 39 and the capillary cavity 40 to divide the first reaction liquid in the capillary cavity 39 by a centrifugal force and return a predetermined amount of the diluted solution to the measurement spot 38, the measurement spot 43 which is formed downstream from the capillary cavity 39 so as to communicate with the capillary cavity 39 through the connection flow path 41, reacts the reagent stored in the measurement spot 43 and the first reaction liquid transferred from the capillary cavity 39 through the connection flow path 41, retains the solution after the reaction, and conducts a second measurement, a capillary cavity 44 which is formed inside, relative to the direction of the axis 102 when viewed from a measurement spot 46, the liquid level of a second reaction liquid retained in the measurement spot 43 acting as an operation cavity and acts as a receiving cavity for collecting the second reaction liquid in the measurement spot 43 after the second reaction liquid is measured, a capillary cavity 64 acting as a third connection section which is formed between the measurement spot 43 and the capillary cavity 44 to stabilize the amount of the second reaction liquid returning to the measurement spot 43, a connection flow path 45 which is formed downstream from the capillary cavity 44 to prevent a second reaction liquid 62 collected in the capillary cavity 44 from flowing into a measurement spot 46, and the measurement spot 46 which is formed downstream from the capillary cavity 44 so as to communicate with the capillary cavity 44 through the connection flow path 45, reacts the reagent stored in the measurement spot 46 and the second reaction liquid transferred from the capillary cavity 44 through the connection flow path 45, retains the solution after the reaction, and conducts a third measurement.

In this configuration, the capillary cavity 39, the capillary cavity 40, the connection flow path 41, the capillary cavity 44, and the connection flow path 45 are 50 μm to 500 μm in cross-sectional dimension in the thickness direction. The dimensions are not particularly limited as long as a capillary force is applied. Moreover, the measurement spot 38, the measurement spot 43, and the measurement spot 46 are 1000 μm to 3000 μm in cross-sectional dimension in the thickness direction. The dimensions can be adjusted according to conditions (including an optical path length, a measured wavelength, the reaction concentration of the sample solution, and the kind of the reagent) for measuring a required amount of the diluted solution and an absorbance.

The following will specifically describe a process of analyzing the sample solution in the device for analysis 1. In the following example, the concentrations of hemoglobin and HbA1c that are contained in blood cells in blood are measured.

FIGS. 14A, 14B to 22A and 22B show the device for analysis 1 set on the rotor 103, from the front side of the rotor 103. A rotation direction C1 indicates a rotation to the left relative to the axis 102 in FIG. 1 and a rotation direction C2 indicates a rotation to the right relative to the axis 102 in FIG. 1.

Figure 14A:
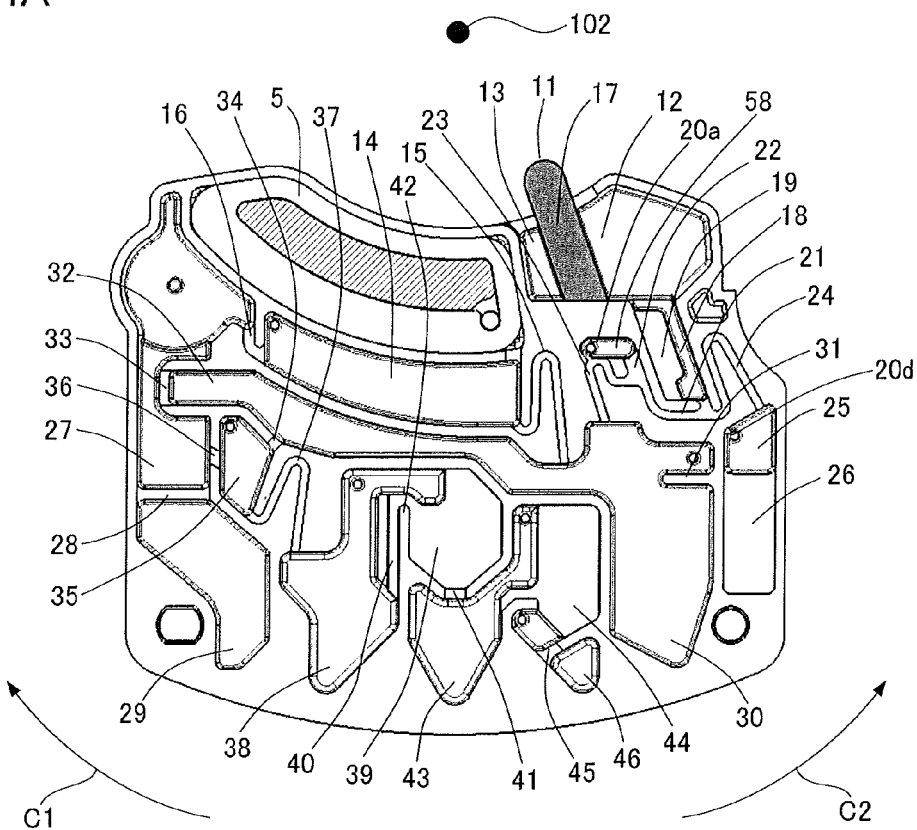
FIG. 14A is an explanatory drawing showing the injection process of the device for analysis according to the embodiment.
Figure 14B:
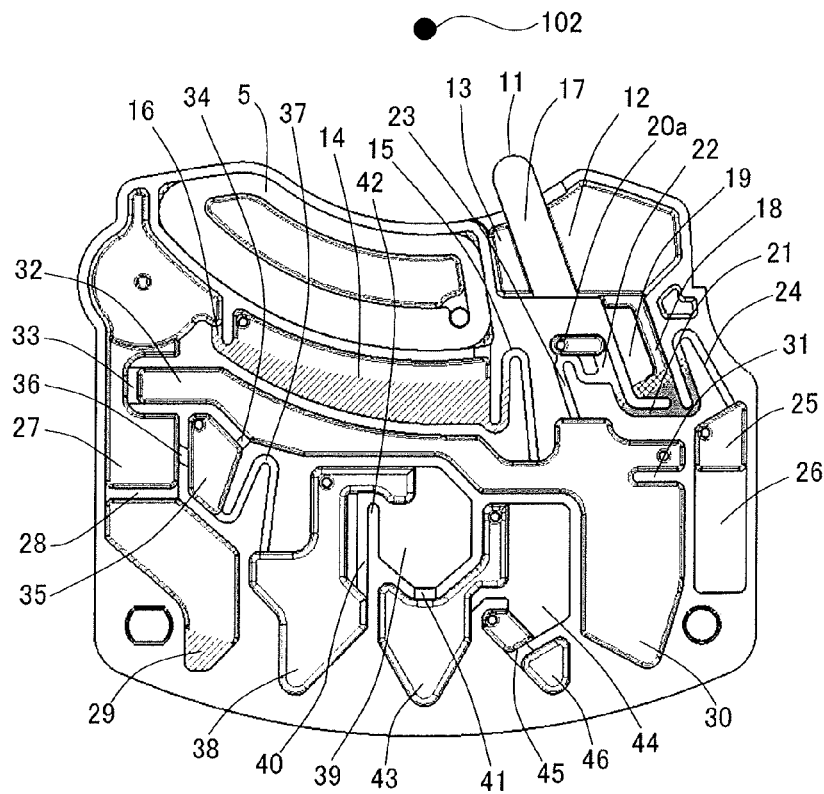
FIG. 14B is an explanatory drawing showing the separation/measurement process of the device for analysis according to the embodiment.

FIGS. 14A and 14B show the injection process and the separation/measurement process of the device for analysis according to the first embodiment of the present invention.

—Step 1—

In FIG. 14A, blood is collected as a sample solution from a puncture of a fingertip and so on through the inlet 11 of the device for analysis 1 by the capillary force of the capillary cavity 17 until the capillary cavity 17 is filled with the blood. In this configuration, the sample solution, for example, about 10 μL of blood can be measured by a volume determined by the clearance and the opposing area of the capillary cavity 17. The shape and dimensions of the capillary cavity 17 may be specified according to an amount required for analysis to adjust a collectable amount.

The device for analysis 1 having collected the required amount of blood is mounted on the rotor 103 of the analyzing apparatus 100 and the opening device of the diluting unit 5 performs an opening operation.

—Step 2, Step 3—

After the opening of the diluting unit 5 is completed, the rotor 103 is rotated (rotation to the right denoted as C2 at 3000 rpm), so that the blood and the diluent in the capillary cavity 17 are transferred to the separation cavity 18 as shown in FIG. 14B. The diluent in the diluting unit 5 is transferred to the retaining cavity 14. When the blood is diluted to collect measured constituents in blood cells, the blood transferred to the separation cavity 18 is separated into plasma constituents and blood cell constituents by a centrifugal force and high hematocrit blood on the outer periphery is collected and diluted, thereby reducing variations in dilution affected by a hematocrit (a ratio of blood cell constituents contained in the blood) varying among individuals.

When the diluent transferred to the retaining cavity 14 during the rotation exceeds a specified amount, the diluent flows into the measurement spot 29 through the overflow path 16, the overflow cavity 27, and the capillary portion 28 and is retained therein.

FIGS. 15A to 15D show the centrifugation in the separation cavity 18 having the capillary cavity 19 and a flow of transfer to the operation cavity 30 through the measurement flow path 23.

Figure 15A:
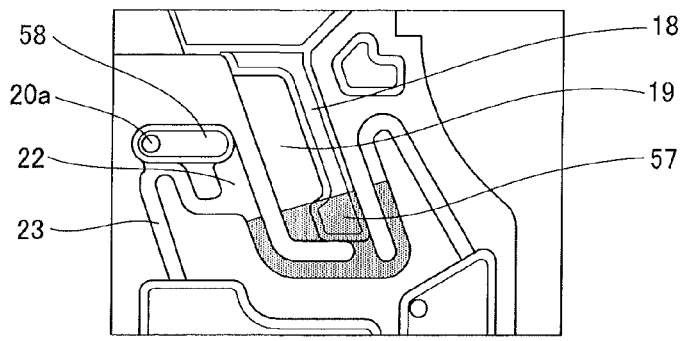
FIG. 15A is an explanatory drawing showing an action of a separation cavity 18 having a capillary cavity 19 according to the embodiment.
Figure 15B:
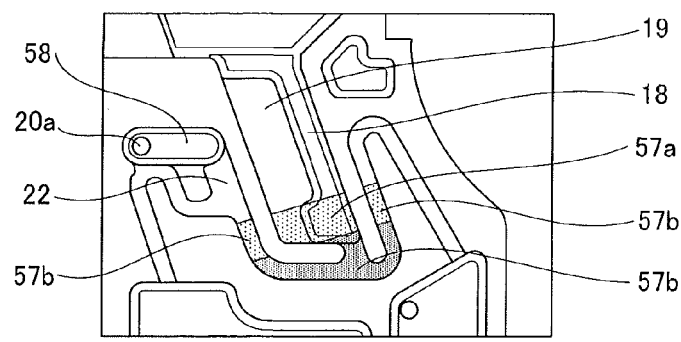
FIG. 15B is an explanatory drawing showing an action of the separation cavity 18 having the capillary cavity 19 according to the embodiment.
Figure 15C:
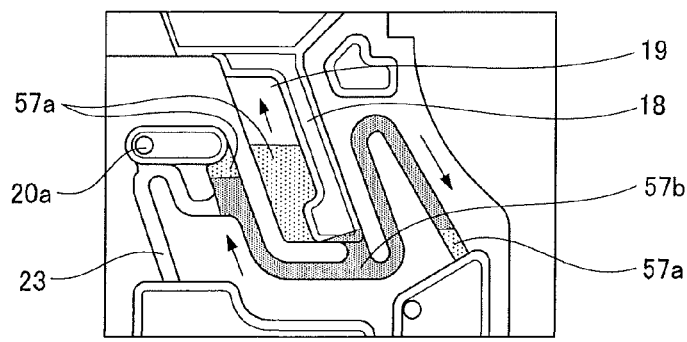
FIG. 15C is an explanatory drawing showing an action of the separation cavity 18 having the capillary cavity 19 according to the embodiment.
Figure 15D:
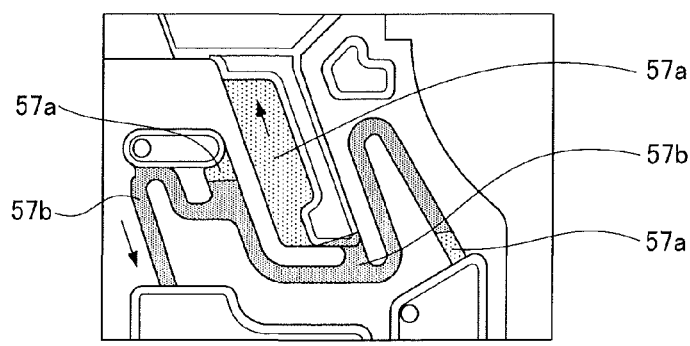
FIG. 15D is an explanatory drawing showing an action of the separation cavity 18 having the capillary cavity 19 according to the embodiment.

Blood 57 retained on the bottom of the separation cavity 18 as shown in FIG. 15A is separated into plasma constituents 57a and blood cell constituents 57b by a centrifugal force as shown in FIG. 15B. When the rotation is stopped and the centrifugal force is eliminated, as shown in FIG. 15C, the plasma constituents 57a in the separation cavity 18 are transferred by capillary action to the capillary cavity 19, and the plasma constituents 57a and the blood cell constituents 57b in the connection flow path 21 are transferred by capillary action to the overflow path 22 connected to a cavity 58 having the air hole 20a communicating with the atmosphere. The plasma constituents 57a and the blood cell constituents 57b in the connection flow path 24 are transferred by capillary action to the overflow cavity 26 having the air hole 20d communicating with the atmosphere. In this configuration, one end of the measurement flow path 23 is connected to the connection flow path 21 at a point where the blood cell constituents 57b reach. As shown in FIG. 15D, only a required amount of the blood cell constituents 57b is transferred from the connection flow path 21 by the capillary force of the measurement flow path 23.

Figure 16A:
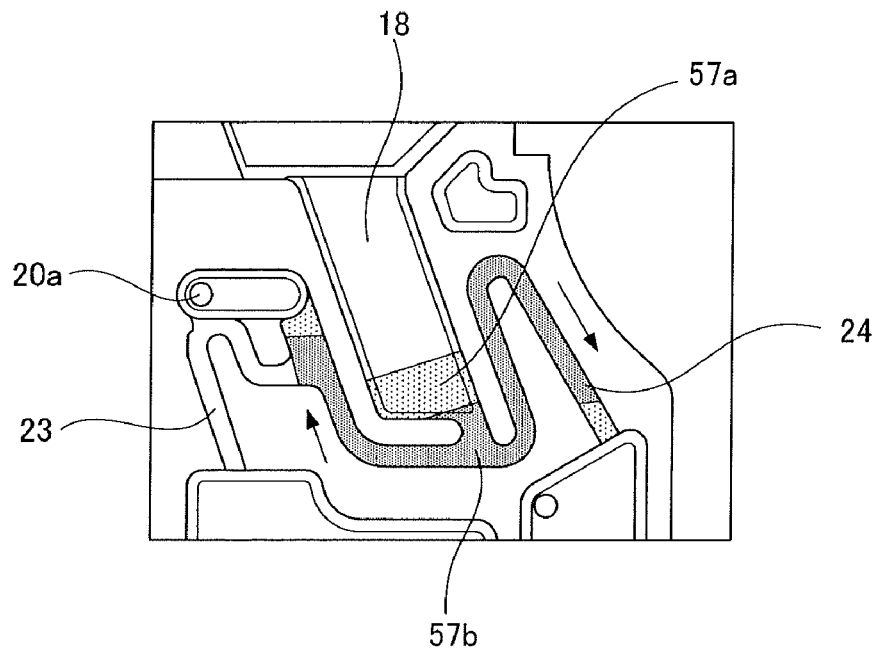
FIG. 16A is an explanatory drawing showing an action of a separation cavity 18 not having a capillary cavity 19 according to a comparative example.
Figure 16B:
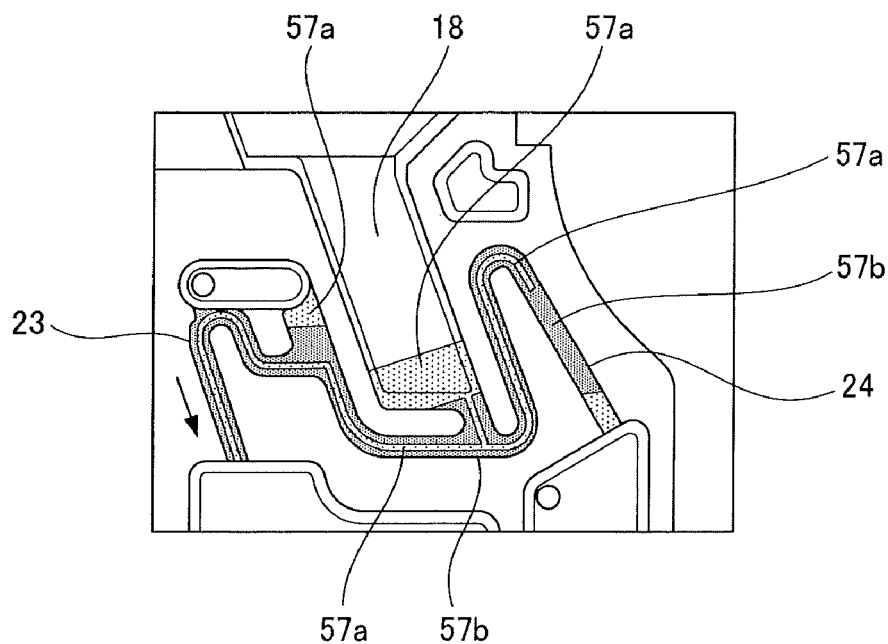
FIG. 16B is an explanatory drawing showing an action of the separation cavity 18 not having the capillary cavity 19 according to the comparative example.

In the present embodiment, since the capillary cavity 19 is formed in the separation cavity 18, most of the plasma constituents 57a remaining in the separation cavity 18 can be retained in the capillary cavity 19. This configuration is useful for transferring only a required amount of the blood cell constituents 57b to the measurement flow path 23 by capillary action. To be specific, in a comparative example where the capillary cavity 19 is not formed in the separation cavity 18 as shown in FIG. 16A, the plasma constituents 57a are retained on the bottom of the separation cavity 18. When the plasma constituents 57a are transferred by the capillary force of the measurement flow path 23, the plasma constituents 57a retained on the bottom of the separation cavity 18 are mixed, as shown in FIG. 16B, into the measurement flow path 23 from the connection flow path 21, so that the required amount of the blood cell constituents 57b cannot be obtained.

On the other hand, the diluent transferred to the retaining cavity 14 is discharged into the overflow cavity 27 through the overflow path 16 when the level of the retained liquid exceeds the connection position of the overflow path 16 and the overflow cavity 27. Thus only a specified amount of the diluent is retained in the retaining cavity 14. In this configuration, the connection flow path 15 is shaped like a siphon having a bent tube disposed inside the connection position of the overflow path 16 and the overflow cavity 27 relative to the radial direction, so that the diluent can be retained in the retaining cavity 14 during the rotation of the device for analysis 1.

Further, since the overflow path 16 connecting the retaining cavity 14 and the overflow cavity 27 is a capillary tube, a capillary force can prevent the diluent from flowing from the retaining cavity 14 into the overflow cavity 27 due to an inertial force and a surface tension when the device for analysis 1 decelerates and stops, so that the diluent can be measured with high accuracy.

—Step 4—

Figure 17A:
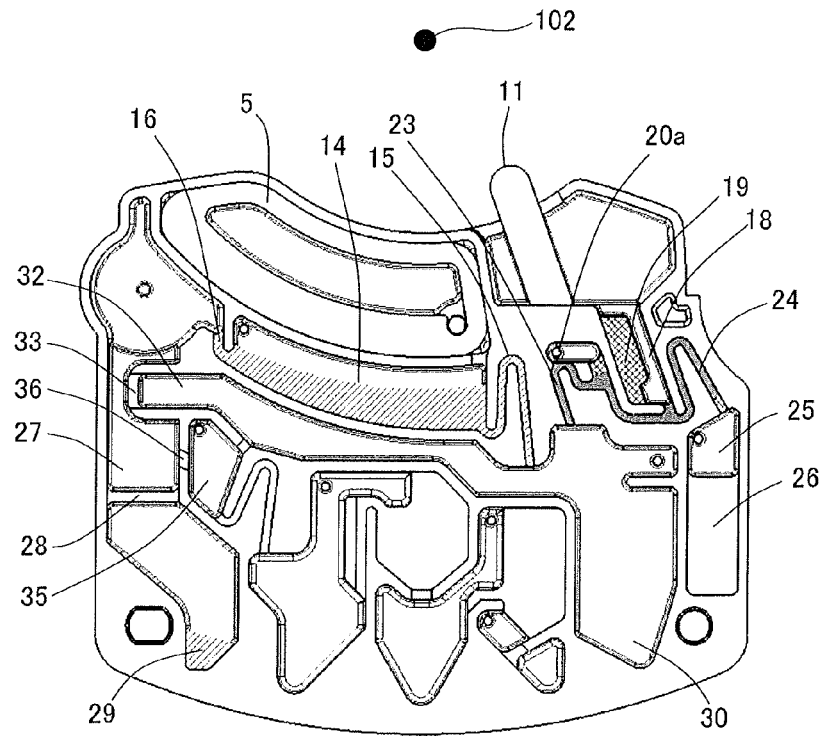
FIG. 17A is an explanatory drawing showing a measuring process of the device for analysis according to the embodiment.
Figure 17B:
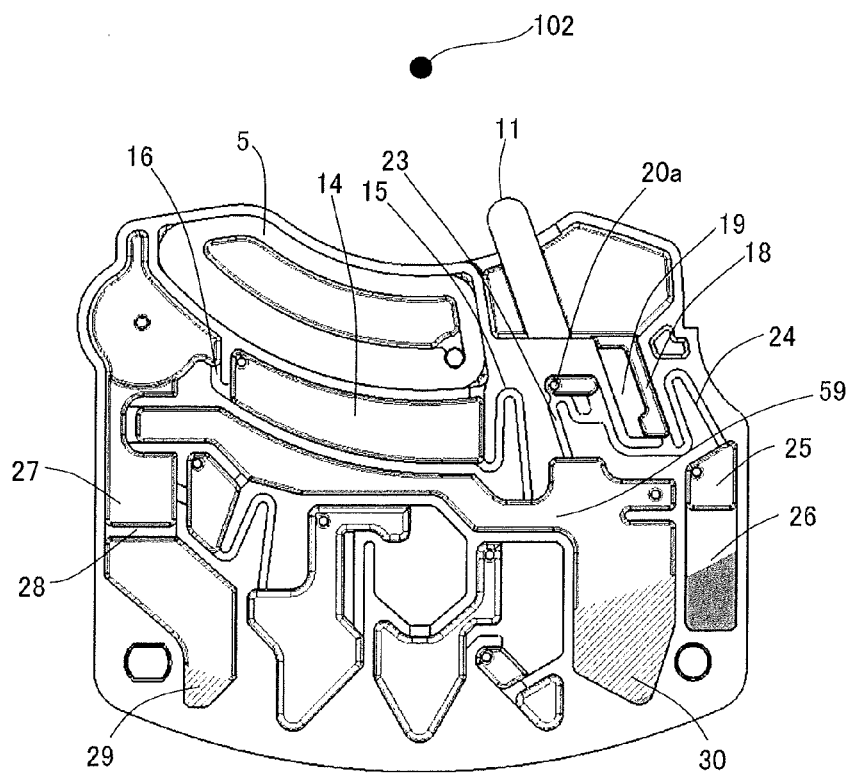
FIG. 17B is an explanatory drawing showing a mixing process of the device for analysis according to the embodiment.

After the rotation (the rotation to the right indicated by C2, at 3000 rpm) of the rotor 103 is stopped and the rotor 103 comes to rest, the rotor 103 is rotated (the rotation to the right indicated by C2, at 2000 rpm) from FIG. 17A, so that the required amount of the blood cell constituents 57b retained in the measurement flow path 23 and the diluent in the retaining cavity 14 flow into the operation cavity 30, are mixed therein, and are diluted therein. An excessive amount of the blood cell constituents 57b is retained in the overflow cavity 26 as shown in FIG. 17B. After that, the optical measuring device 109 performs reference measurement for reading when the diluent in the measurement spot 29 of the device for analysis 1 is located between the laser light source 105 and the photodetector 106. At this point, the reference measurement is performed while switching the wavelength of the laser light source 105 between 535 nm and 625 nm.

—Step 5—

Figure 18A:
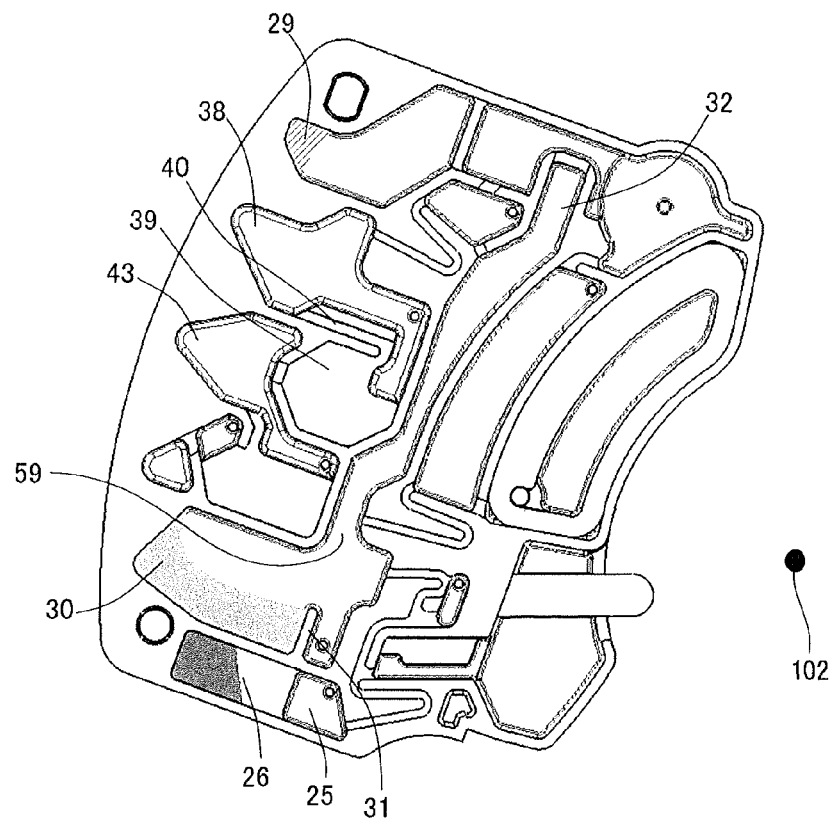
FIG. 18A is an explanatory drawing showing the mixing process of the device for analysis according to the embodiment.
Figure 18A:

Next, the device for analysis 1 is set at around 60° as shown in FIG. 18A and the diluent is stirred by controlling the motor 104 at a frequency of 1000 rpm so as to swing the device for analysis 1 by about ±1 mm.

—Step 6—

Figure 18B:
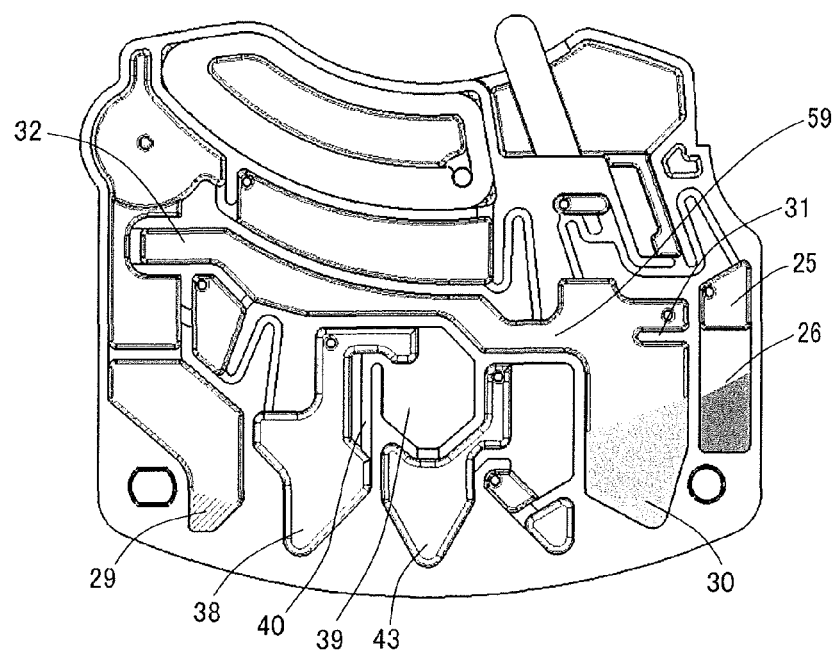
FIG. 18B is an explanatory drawing showing the mixing process of the device for analysis according to the embodiment.

After that, the device for analysis 1 is set at around 180° as shown in FIG. 18B and the diluent is stirred by controlling the motor 104 at a frequency of 1000 rpm so as to swing the device for analysis 1 by about ±1 mm.

In this configuration, the operation cavity 30 and the retaining cavity 32 are connected via a connection section 59. The connection section 59 during stirring is located inside the liquid level of the diluted solution retained in the operation cavity 30, relative to the rotation axis 102 for generating a centrifugal force, so that the diluent does not flow into the retaining cavity 32 during stirring and mixing.

—Step 7—

Figure 19A:
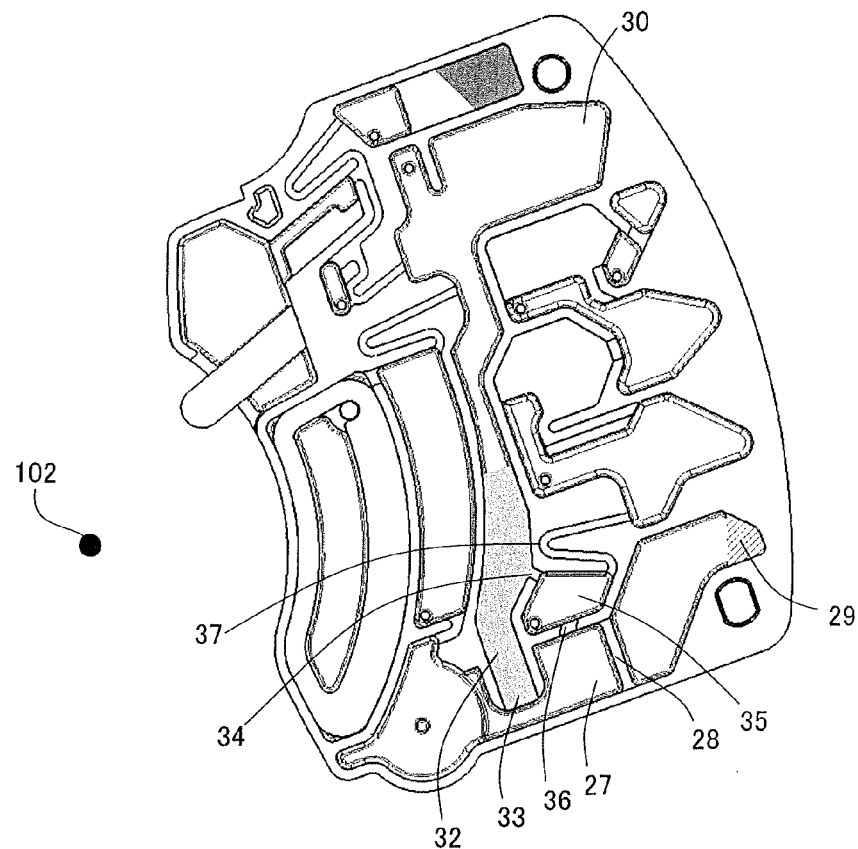
FIG. 19A is an explanatory drawing showing a transfer process of a diluted solution of the device for analysis according to the embodiment.

Next, the device for analysis 1 is set at around 300° as shown in FIG. 19A, the motor 104 is controlled at a frequency of 1000 rpm so as to swing the device for analysis 1 by about ±1 mm, and the diluted blood cell constituents 57b (diluted solution) of the operation cavity 30 are swingingly transferred to the retaining cavity 32 through the connection section 59.

In this configuration, even when the device for analysis 1 is moved to a position around 300° as shown in FIG. 19A, the diluted solution retained in the operation cavity 30 is held by a surface tension applied to the wall surface of the operation cavity 30 (because the surface tension is larger than a force of gravity applied to the diluted solution). The device for analysis 1 is swung to apply an inertial force to the diluted solution, so that the inertial force and the force of gravity that are applied to the diluted solution exceed the surface tension applied to the wall surface of the operation cavity 30 and thus allow the diluted solution to be transferred to the retaining cavity 32.

—Step 8—

Figure 19B:
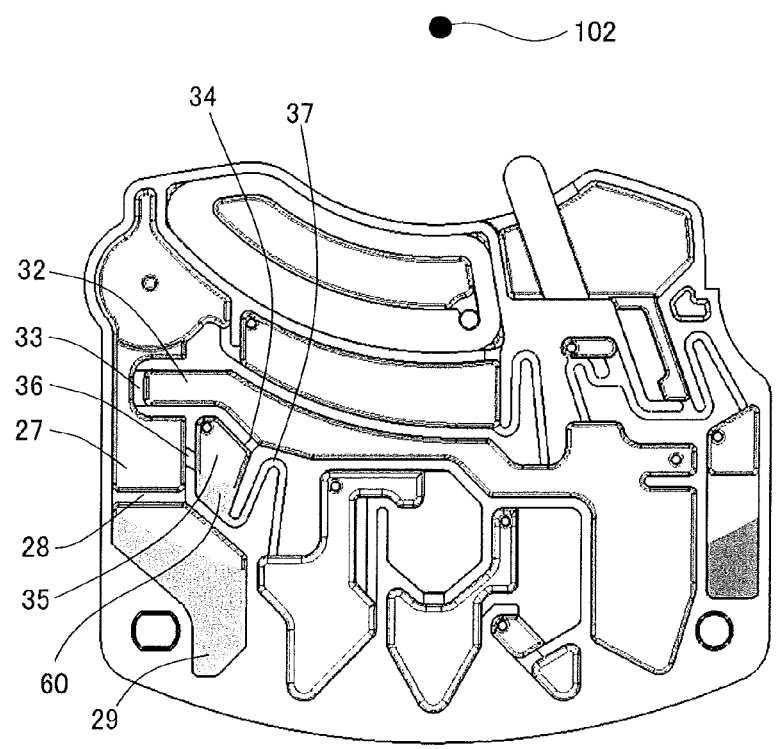
FIG. 19B is an explanatory drawing showing the measuring process of the device for analysis according to the embodiment.

Next, the device for analysis 1 is rotated (the rotation to the right indicated by C2, at 2000 rpm) by the rotor 103, so that as shown in FIG. 19B, the specific amount of the diluted solution is transferred from the retaining cavity 32 to the retaining cavity 35 through the connection flow path 34. When the diluted solution transferred to the retaining cavity 35 exceeds the predetermined amount, an excessive amount of the diluted solution flows into the overflow cavity 27 through the overflow path 36, so that only the specified amount of a diluted solution 60 is retained in the retaining cavity 35.

—Step 9, Step 10—

Figure 20A:
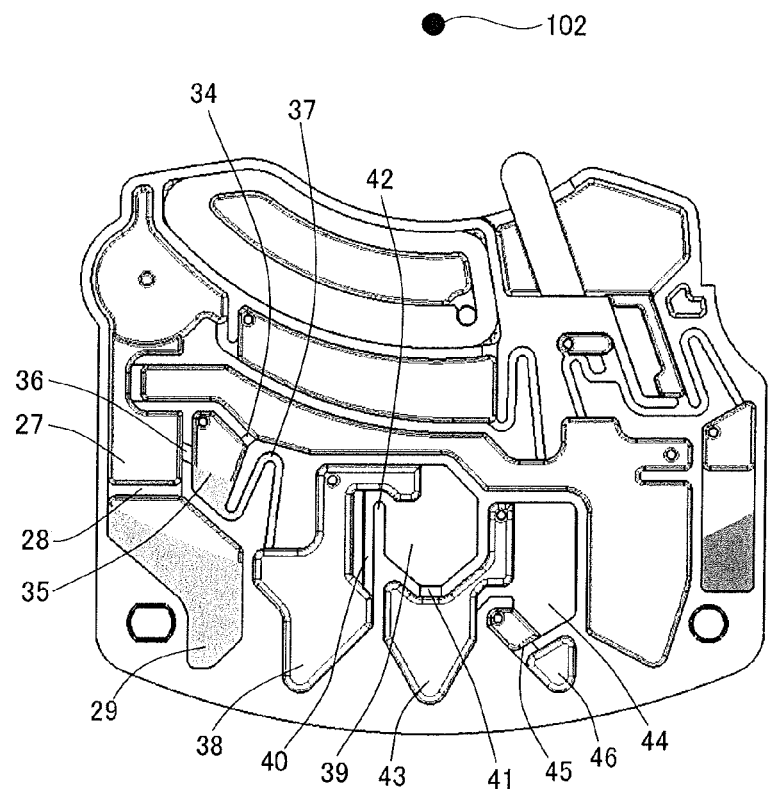
FIG. 20A is an explanatory drawing showing a transfer process of the device for analysis according to the embodiment.

The rotation of the rotor 103 (the rotation to the right indicated by C2, at 2000 rpm) is stopped and the rotor 103 comes to rest, so that the connection flow path 37 is primed with the diluted solution of the retaining cavity 35 as shown in FIG. 20A. Further, the rotor 103 is rotated (the rotation to the left indicated by C2, at 2000 rpm) from FIG. 20A, so that the specified amount of the diluted solution retained in the retaining cavity 35 is transferred to the measurement spot 38 through the connection flow path 37 and dissolves the denatured reagent retained in the measurement spot 38 beforehand.

—Step 11—

Figure 20B:
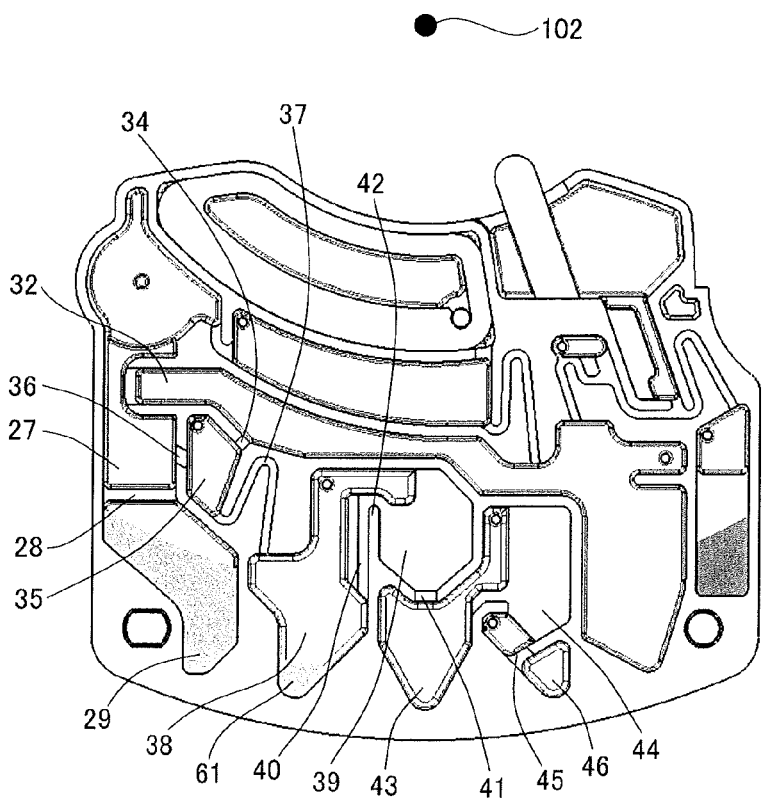
FIG. 20B is an explanatory drawing showing a reagent reaction/measuring process of the device for analysis according to the embodiment.

After that, at around 180° as shown in FIG. 20B, the motor 104 is controlled at a frequency of 1000 rpm so as to swing the device for analysis 1 by about ±1 mm, so that a first reaction liquid 61 in the measurement spot 38 of the device for analysis 1 is stirred.

In this configuration, the measurement spot 38 and the measurement spot 43 communicate with each other through the capillary cavity 40 and the capillary cavity 39. In this case, the capillary cavity 40 acts as a second connection section and the capillary cavity 40 during stirring is located inside the liquid level of the diluted solution retained in the measurement spot 38, relative to the rotation axis 102 for generating a centrifugal force, so that the diluent does not flow into the capillary cavity 39 on the side of the measurement spot 43 during stirring and mixing.

—Step 12, Step 13—

Next, the device for analysis 1 is rested and the first reaction liquid 61 is subjected to reaction of degeneration, and then the rotor 103 is rotated (the rotation to the left indicated by C1, at 1500 rpm) to perform the first measurement.

In the first measurement, reading is performed when the first reaction liquid 61 having been subjected to reaction of degeneration in the measurement spot 38 of the device for analysis 1 is located between the laser light source 105 and the photodetector 106 in an emitting state where the wavelength of the laser light source 105 is switched to 535 nm. The arithmetic section 110 displays a denatured hemoglobin concentration on the display section 111. The denatured hemoglobin concentration is obtained by digitizing a measured value of the first measurement based on a reference value obtained by reading the measurement spot 29 beforehand with the laser light source 105 having a wavelength of 535 nm.

In this case, "denaturation" is to remove (expose) specific points out of the structure of protein. An antigen-antibody reaction, which will be described later, is brought about by a latex reagent reacting specifically to a "denatured region" which is a region exposed out of the structure of protein.

—Step 14—

Figure 21A:
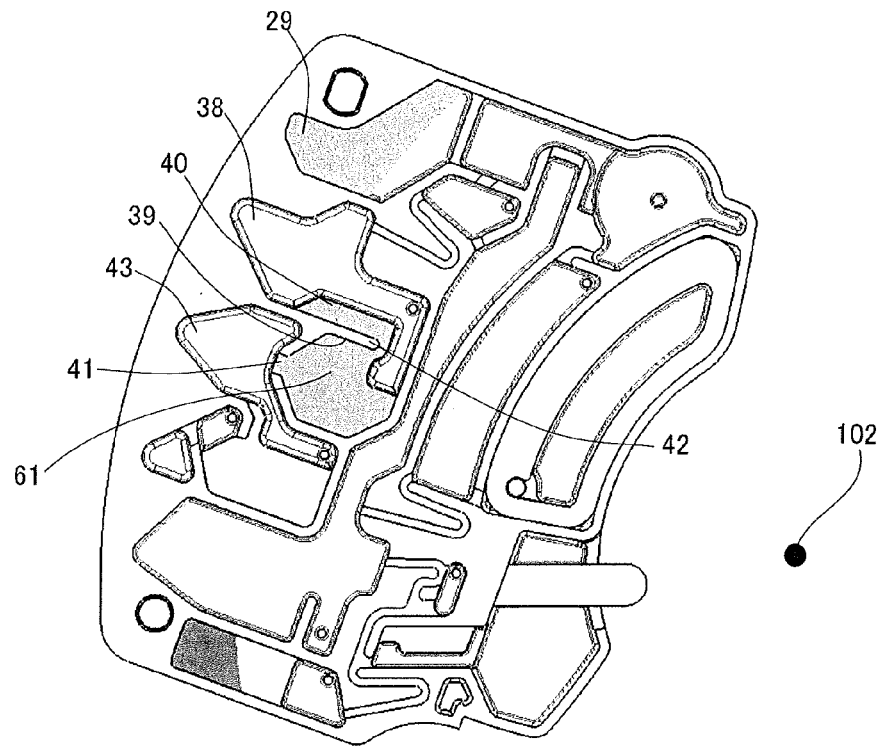
FIG. 21A is an explanatory drawing showing the transfer process of the device for analysis according to the embodiment.

Next, the device for analysis 1 is set at around 60° as shown in FIG. 21A and the motor 104 is controlled at a frequency of 1500 rpm so as to swing the device for analysis 1 by about ±1 mm, so that the first reaction liquid 61 retained in the measurement spot 38 is transferred to the capillary cavity 39 by capillary action and a specific amount of the first reaction liquid 61 is retained in the capillary cavity 39.

—Step 15—

Next, the rotor 103 is rotated (the rotation to the left indicated by C1, at 2000 rpm), so that the first reaction liquid 61 flows into the measurement spot 43 from the capillary cavity 39 through the connection flow path 41 and dissolves the latex reagent retained in the measurement spot 43 beforehand.

—Step 16—

Figure 21B:
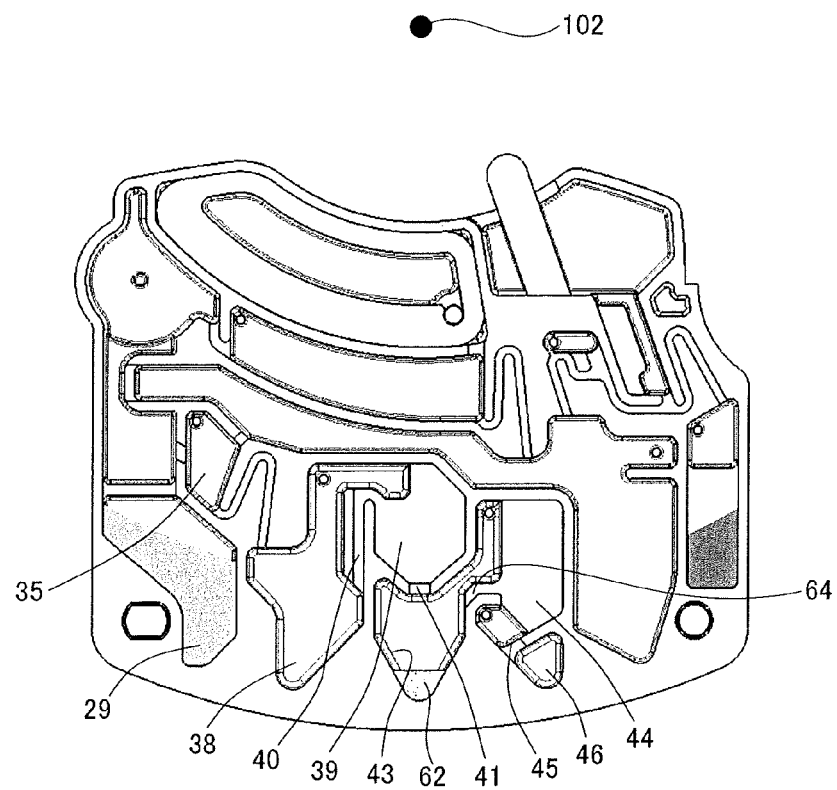
FIG. 21B is an explanatory drawing showing the reagent reaction/measuring process of the device for analysis according to the embodiment.

After that, at around 180° as shown in FIG. 21B, the motor 104 is controlled at a frequency of 1000 rpm so as to swing the device for analysis 1 by about ±1 mm, so that the second reaction liquid 62 in the measurement spot 43 of the device for analysis 1 is stirred.

In this configuration, the measurement spot 43 and the measurement spot 46 communicate with each other through the capillary cavity 44, and the capillary cavity 64 connecting the measurement spot 43 and the capillary cavity 44 is located during stirring inside the liquid level of the diluted solution retained in the measurement spot 43, relative to the rotation axis 102 for generating a centrifugal force, so that the diluted solution does not flow into the capillary cavity 44 on the side of the measurement spot 46 during stirring and mixing.

—Step 17, Step 18—

Next, the device for analysis 1 is rested, the second reaction liquid 62 is subjected to an antigen-antibody reaction, and then the rotor 103 is rotated (the rotation to the left indicated by C1, at 1500 rpm) to perform a second measurement.

In the second measurement, reading is performed when the second reaction liquid 62 having been subjected to the antigen-antibody reaction in the measurement spot 43 of the device for analysis 1 is located between the laser light source 105 and the photodetector 106 in an emitting state where the wavelength of the laser light source 105 is switched to 625 nm.

—Step 19—

Figure 22A:
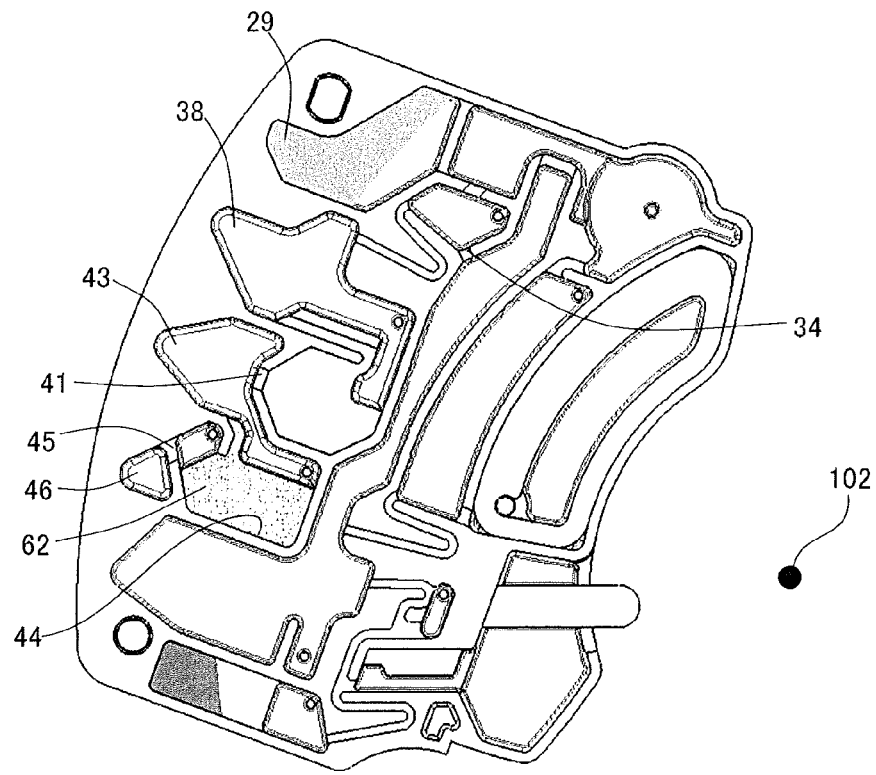
FIG. 22A is an explanatory drawing showing the transfer process of the device for analysis according to the embodiment.

Next, the device for analysis 1 is set at around 60° as shown in FIG. 22A and the motor 104 is controlled at a frequency of 1500 rpm so as to swing the device for analysis 1 by about ±1 mm, so that the second reaction liquid 62 is transferred to the capillary cavity 44 by capillary action.

—Step 20—

After that, the rotor 103 is rotated (the rotation to the left indicated by C1, at 2000 rpm), so that a specified amount of the second reaction liquid 62 retained in the capillary cavity 44 flows into the measurement spot 46 through the connection flow path 45 and dissolves a coagulation reagent retained in the measurement spot 46.

—Step 21—

Figure 22B:
FIG. 22B is an explanatory drawing showing the reagent reaction/measuring process of the device for analysis according to the embodiment.
Figure 22B:
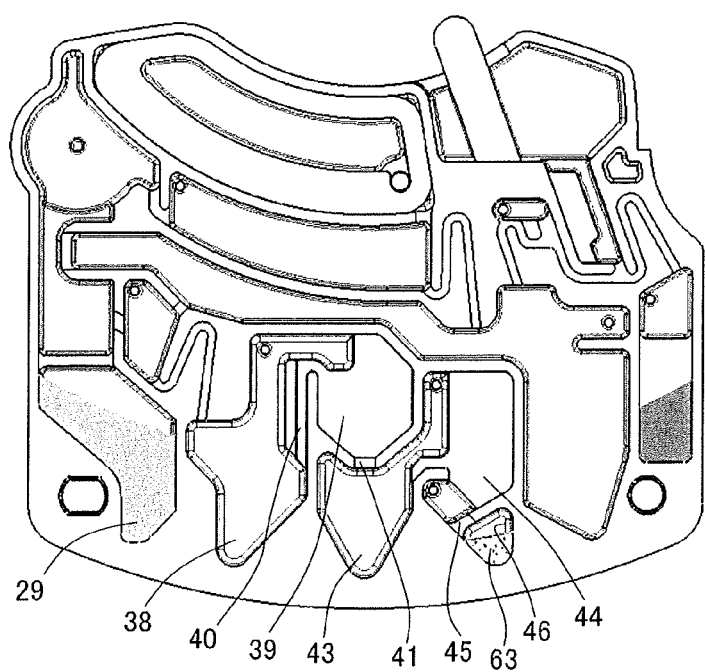
Figure 23:
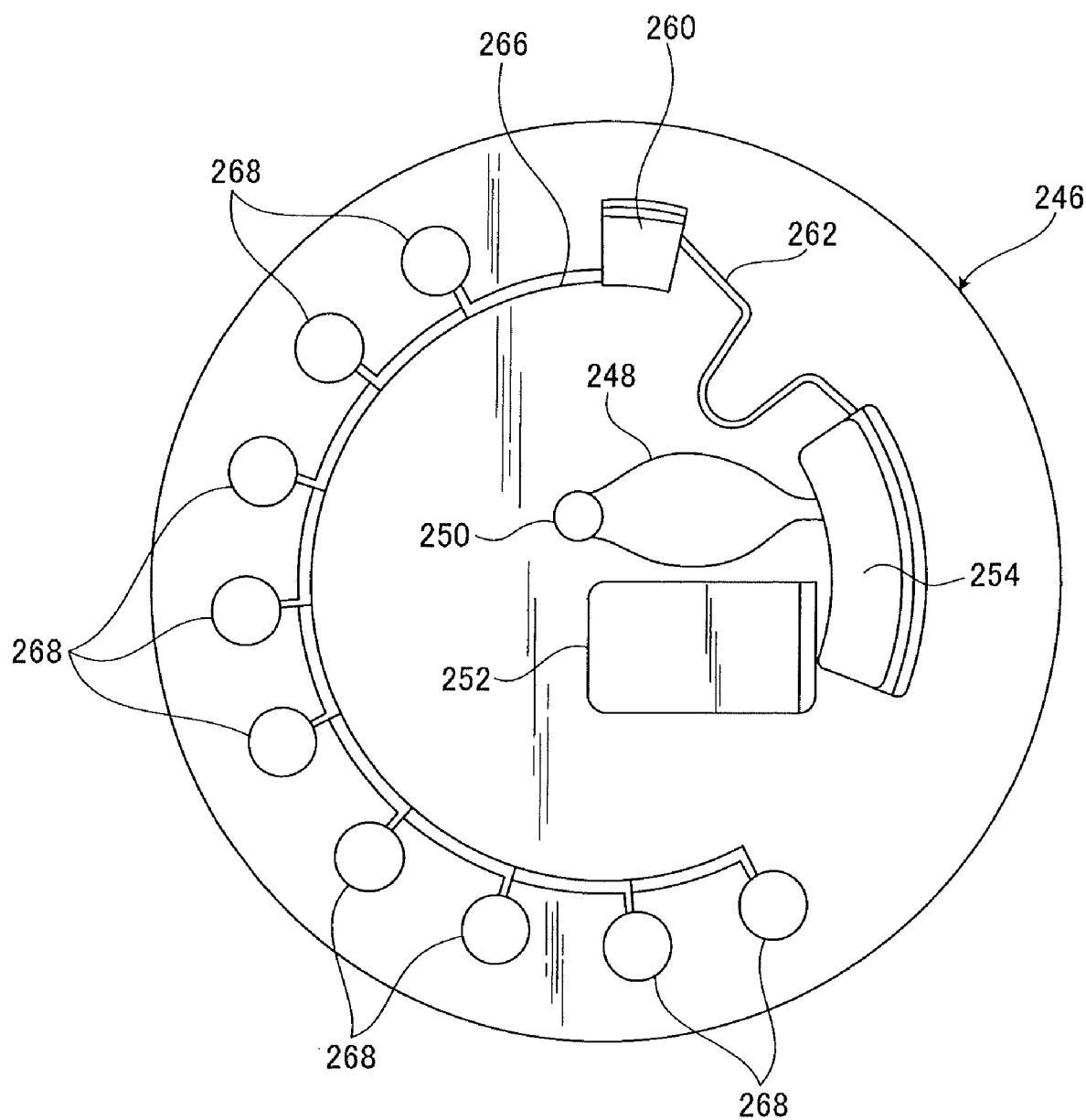
FIG. 23 is a plan view showing a device for analysis according to the prior art.

After that, at around 180° as shown in FIG. 22B, the motor 104 is controlled at a frequency of 1000 rpm so as to swing the device for analysis 1 by about ±1 mm, so that a third reaction liquid 63 in the measurement spot 46 of the device for analysis 1 is stirred.

—Step 22, Step 23—

Next, the device for analysis 1 is rested, the third reaction liquid 63 is subjected to an agglutination reaction, and then the rotor 103 is rotated (the rotation to the left indicated by C1, at 1500 rpm) to perform a third measurement.

In the third measurement, reading is performed when the third reaction liquid 63 having been subjected to the agglutination reaction in the measurement spot 46 of the device for analysis 1 is located between the laser light source 105 and the photodetector 106 in an emitting state where the wavelength of the laser light source 105 is switched to 625 nm. The arithmetic section 110 displays an HbA1c concentration and an HbA1c % value on the display section 111. The HbA1c concentration is obtained by digitizing a measured value of the second and third measurements based on a reference value obtained by reading the measurement spot 29 beforehand with the laser light source 105 having a wavelength of 625 nm. The HbA1c % value is calculated based on the denatured hemoglobin concentration.

In the part of the operation cavity 30 and the retaining cavity 32, the retaining cavity 32 is equivalent to the receiving cavity of claim 1.

In the part of the measurement spot 38 and the capillary cavity 39, the measurement spot 38 is equivalent to the operation cavity of claim 1 and the capillary cavity 39 is equivalent to the receiving cavity of claim 1.

In the part of the measurement spot 43 and the capillary cavity 44, the measurement spot 43 is equivalent to the operation cavity of claim 1 and the capillary cavity 44 is the receiving cavity of claim 1.

INDUSTRIAL APPLICABILITY

According to the present invention, all solutions transferred at different times can be retained in the same location and can be transferred to the subsequent process at a necessary time, so that the solutions can be transferred to the subsequent process after completely mixed and the accuracy of analysis can be improved. Thus the present invention is useful as a transfer controller of a device for analysis which is used for analyzing the components of a liquid collected from an organism and the like.

The invention claimed is:

1. A device for analysis having a micro channel structure for transferring a solution to a measurement spot by a centrifugal force and being used for reading in which a reaction liquid at the measurement spot is optically accessed, the device comprising:
an operation cavity and a receiving cavity which are arranged from an upstream side to a downstream side of the transfer; and
a connection section for communicating the operation cavity and the receiving cavity to transfer a solution in the operation cavity to the receiving cavity, the connection section being located inside a liquid level of the solution retained in the operation cavity, relative to a rotation axis for generating the centrifugal force.

2. The device for analysis according to claim 1, wherein the receiving cavity is formed with a cross-sectional dimension in a thickness direction for generating a capillary force and a specified amount of the solution is collected by the capillary force.

3. The device for analysis according to claim 1, wherein the receiving cavity collects a predetermined amount of the solution by a force of gravity generated by inclination.

4. The device for analysis according to claim 1, wherein the receiving cavity collects a predetermined amount of the solution by an inertial force generated by swinging and a force of gravity generated by inclination.

5. An analyzing apparatus in which the device for analysis having collected a sample solution according to claim 1 is set, comprising:
   a rotation driving device for rotating the device for analysis about the axis; and
   an analyzing device for conducting an analysis by optically accessing the solution in the device for analysis which has been transferred by the rotation driving device,
   wherein the axis is inclined and the solution retained in the operation cavity is transferred to the receiving cavity by an inertial force and a force of gravity.

6. An analyzing apparatus, in which the device for analysis having collected a sample solution according to claim 1 is set, comprising:
   a rotation driving device for rotating the device for analysis about the axis; and
   an analyzing device for conducting an analysis by optically accessing the solution in the device for analysis which has been transferred by the rotation driving device,
   wherein the axis is inclined and the solution retained in the operation cavity is transferred to the connection section of the operation cavity and the receiving cavity by a force of gravity.

7. An analyzing apparatus, in which the device for analysis having collected a sample solution according to claim 1 is set, comprising:
   a rotation driving device for rotating the device for analysis about the axis; and
   an analyzing device for conducting an analysis by optically accessing the solution in the device for analysis which has been transferred by the rotation driving device,
   wherein the axis is inclined and the solution retained in the operation cavity is transferred to the receiving cavity by a force of gravity.

8. An analyzing apparatus, in which the device for analysis having collected a sample solution according to claim 1 is set, comprising:
   a rotation driving device for rotating the device for analysis about the axis; and
   an analyzing device for conducting an analysis by optically accessing the solution in the device for analysis which has been transferred by the rotation driving device,
   wherein the axis is inclined and the solution retained in the operation cavity is transferred to the connection section of the receiving cavity by an inertial force and a force of gravity.

9. The analyzing apparatus according to claim 5, wherein the device for analysis is movable to a position where the connection section of the receiving cavity and the operation cavity is located under the operation cavity when viewed from a front of the device for analysis.

10. The analyzing apparatus according to claim 5, wherein the axis is inclined and the device for analysis is swung about the axis at a position where the connection section is located under the operation cavity when viewed from a front of the device for analysis.

11. The analyzing apparatus according to claim 5, wherein the device for analysis is swung about the axis at any rotational position.

12. The analyzing apparatus according to claim 5, wherein the axis has an angle of inclination that is optionally settable.

13. The analyzing apparatus according to claim 5, wherein the axis has an angle of inclination of 0° to 45°.

14. An analyzing method using the device for analysis according to claim 1, comprising:
   setting the device for analysis on a rotor having an axis inclined by a predetermined angle, rotating the rotor to transfer, to the operation cavity, a diluent and a sample solution applied to the device for analysis and mix the diluent and the sample solution;
   moving the rotor such that the connection section of the receiving cavity and the operation cavity of the device for analysis is located under the operation cavity when viewed from a front of the device for analysis, and vibrating the device for analysis at a stop position to swingingly transfer a diluted solution having been diluted by the mixing to a downstream side of a transfer path;
   rotating the rotor to collect a fixed amount of the diluted solution, dissolving a reagent stored at the measurement spot with the solution received at the measurement spot after the swinging transfer performed by rotating the rotor or vibrating the device for analysis, and stirring the reagent; and
   rotating the rotor to optically access the reaction liquid at the measurement spot when the measurement spot is located at a reading position.

15. The analyzing method according to claim 14, further comprising: rotating the rotor to collect the fixed amount of the diluted solution, repeating the swinging transfer, in which the rotor is rotated or the device for analysis is vibrated, to sequentially transfer the reaction liquid to the measurement spots on the downstream side out of the plurality of measurement spots connected in series along the transfer path; and
   conducting a measurement by optically accessing the measurement spot every time the reaction liquid reaches the measurement spot.

16. A device for analysis having a micro channel structure for transferring a solution by a centrifugal force,
   the device comprising:
   a first retaining section for retaining a sample solution;
   a second retaining section for retaining a diluent;
   a third retaining section for receiving the sample solution and the diluent from the first and second retaining sections;
   a fourth retaining section which communicates with the third retaining section through a connection section and receives a diluted solution from the third retaining section; and
   a measurement spot which is formed on a downstream side of the transfer from the fourth retaining section, retains a reagent, and retains a reaction liquid obtained by a reaction after the reagent is dissolved by the diluted solution received from the fourth retaining section,
   wherein the reaction liquid at the measurement spot is optically accessed for reading and the connection section for communicating the third retaining section and the fourth retaining section is located inside a liquid level of the diluted solution retained in the third retaining section, relative to a rotation axis for generating the centrifugal force.

17. The device for analysis according to claim 16, further comprising: between the fourth retaining section and the measurement spot, a retaining cavity which receives the diluted solution from the fourth retaining section through a connection flow path and retains a specified amount of the diluted solution;

a connection flow path for communicating the retaining cavity and the measurement spot; and a second measurement spot which is formed on the downstream side of the transfer from the measurement spot, retains the reagent, and retains the reaction liquid obtained by the reaction after the reagent is dissolved by the solution received from the measurement spot, wherein a second connection section for communicating the measurement spot and the downstream side of the transfer is located inside the liquid level of the solution retained at the measurement spot, relative to the rotation axis for generating the centrifugal force.

18. The device for analysis according to claim 17, further comprising a third measurement spot which is formed on the downstream side of the transfer from the second measurement spot, retains the reagent, and retains the reaction liquid obtained by the reaction after the reagent is dissolved by the solution received from the second measurement spot, wherein a third connection section for communicating the second measurement spot and the downstream side of the transfer is located inside the liquid level of the solution retained at the second measurement spot, relative to the rotation axis for generating the centrifugal force.

* * * * *